US011011277B1

(12) United States Patent
Kelly et al.

(10) Patent No.: US 11,011,277 B1
(45) Date of Patent: May 18, 2021

(54) HEAT MAPS OF INFECTIOUS AGENTS AND METHODS OF USING SAME TO SCREEN SUBJECTS AND/OR DETERMINE AN INFECTION RISK

(71) Applicants: Sean Kelly, Yorba Linda, CA (US); Kevin M. Kelly, Chesterton, IN (US)

(72) Inventors: Sean Kelly, Yorba Linda, CA (US); Kevin M. Kelly, Chesterton, IN (US)

(*) Notice: Subject to any disclaimer, the term of this patent is extended or adjusted under 35 U.S.C. 154(b) by 0 days.

(21) Appl. No.: 16/890,909

(22) Filed: Jun. 2, 2020

(51) Int. Cl.
*H04Q 5/22* (2006.01)
*G16H 50/80* (2018.01)
*G06Q 50/22* (2018.01)
*G06Q 10/06* (2012.01)

(52) U.S. Cl.
CPC ......... *G16H 50/80* (2018.01); *G06Q 10/0635* (2013.01); *G06Q 50/22* (2013.01)

(58) Field of Classification Search
CPC .. G06F 19/3406; G06F 16/2228; G06F 19/24; A61B 5/7275; G16H 10/20
USPC ................... 340/10.1, 573.1; 435/5; 600/300
See application file for complete search history.

(56) References Cited

U.S. PATENT DOCUMENTS

| | | | | |
|---|---|---|---|---|
| 7,718,354 B2* | 5/2010 | Ecker | ..................... | C12Q 1/701 435/5 |
| 7,817,046 B2* | 10/2010 | Coveley | ................. | G06Q 10/08 340/573.1 |
| 10,251,610 B2* | 4/2019 | Parthasarathy | ...... | A61B 5/0059 |
| 10,394,776 B2* | 8/2019 | Khan | ..................... | G06F 16/904 |
| 10,431,329 B2* | 10/2019 | Kagen | ..................... | G16H 50/30 |
| 2006/0220879 A1* | 10/2006 | Chan | .................. | G06K 17/0022 340/573.1 |
| 2007/0173700 A1* | 7/2007 | Ishihara | ................ | G06T 11/206 600/300 |
| 2014/0167917 A2* | 6/2014 | Wallace | ................. | G16H 70/60 340/10.1 |
| 2017/0024531 A1* | 1/2017 | Malaviya | ............... | G16H 40/63 |
| 2019/0050534 A1* | 2/2019 | Apte | ..................... | G16H 50/70 |

OTHER PUBLICATIONS

Google patents search, Sep. 2, 2020 (Year: 2020).*
ip.com, patents search, Dec. 1, 2020 (Year: 2020).*
ip.com, NPL search, Dec. 1, 2020 (Year: 2020).*
ip.com search, Mar. 22, 2021 (Year: 2021).*

* cited by examiner

*Primary Examiner* — Dilek B Cobanoglu
(74) *Attorney, Agent, or Firm* — Morgan, Lewis & Bockius LLP; Christopher J. Betti

(57) ABSTRACT

The present disclosure provides methods for screening subjects at a subordinate location within a geographic region, or a subordinate space within the subordinate location for an infectious agent. Such methods may comprise assigning a risk score to each of the one or more subordinate locations or subordinate spaces based on an amount of infectious agent in pooled environmental samples and pooled biological samples in a subordinate location or subordinate space as compared to each other subordinate location or subordinate space, and then screening biological samples from subordinate locations or subordinate spaces that have a higher risk score before screening biological samples from subordinate locations or subordinate spaces that have a lower risk score. Methods for determining a risk of a viral infection in one or more geographic regions are also provided.

22 Claims, 6 Drawing Sheets

HEAT MAPS OF INFECTIOUS AGENTS AND METHODS OF USING SAME TO SCREEN SUBJECTS AND/OR DETERMINE AN INFECTION RISK

TECHNICAL FIELD

The present disclosure relates generally to methods for screening subjects and/or assessing a risk of infection from an infectious agent in a geographic region, subordinate locations within the geographic region, or subordinate spaces within a subordinate location.

BACKGROUND

COVID-19 has been declared a pandemic by the World Health Organization (WHO). Emerging viral pandemics such as COVID-19 can place extraordinary and sustained demands on public health systems and on providers of essential services. Inevitably, such demands create the need to ration medical equipment and interventions. And rationing is already here. In the United States, perhaps the earliest example was the near-immediate recognition that there were not enough high-filtration N-95 masks for health care workers, prompting contingency guidance on how to reuse masks designed for single use. Moreover, physicians have proposed directing crucial resources such as intensive care beds and ventilators to patients who can benefit most from treatment.

It is widely recognized that screening is an imperfect barrier to spread of a disease due to the absence of detectable symptoms during the incubation period, variation in the severity and detectability of symptoms once the disease begins to progress, and/or imperfect performance of screening equipment or personnel. Not to mention in the presence of a pandemic there tends to be a great shortage of testing resources. Indeed, three months after SARS-CoV-2 arrived in the United States there is still inadequate access to appropriate diagnostic tests and confusion among healthcare professionals and the public about prioritization of testing and interpretation of results.

Further exacerbating current testing protocols is that in the case of a highly contagious airborne pathogen such as SARS-CoV-2, an infected subject may shed (e.g. exhale) virus into the air which can remain aloft minutes or hours thereafter, infecting unsuspecting subjects who never physically encountered or saw the infected individual. Virus may also be transported through HVAC systems or tidal air movements to other areas within a space or building. Complicating traceability further still, a person is contagious generally one to three days before onset of symptoms, making behavioral preventive measures nearly impossible. As such, there exists a need for improved methods to test and screen for infectious agents such as SARS-CoV-2.

SUMMARY

The present disclosure solves the above need by the use of sample pooling, wherein a plurality of samples are aggregated into a lesser number. Such pooling dramatically reduces the time, resources, and/or cost of screening/testing.

The present disclosure provides methods for screening biological samples obtained from subjects at a subordinate location within a geographic region, or a subordinate space within the subordinate location for an infectious agent by dividing the geographic region into one or more subordinate locations or dividing the subordinate locations into one or more subordinate spaces; pooling environmental samples obtained within each of the one or more subordinate locations or subordinate spaces; pooling biological samples obtained from subjects within each of the one or more subordinate locations or subordinate spaces; measuring an amount of the infectious agent in the pooled environmental samples and pooled biological samples for each of the one or more subordinate locations or subordinate spaces; assigning an risk score to each of the one or more subordinate locations or subordinate spaces based on the amount of infectious agent in the pooled environmental samples and the pooled biological samples in a subordinate location or subordinate space as compared to each other subordinate location or subordinate space; and screening biological samples from subordinate locations or subordinate spaces that have a higher risk score before screening biological samples from subordinate locations or subordinate spaces that have a lower risk score.

The present disclosure provides methods for screening biological samples obtained from subjects at a subordinate location within a geographic region, or a subordinate space within the subordinate location for an infectious agent by dividing the geographic region into one or more subordinate locations or dividing the subordinate locations into one or more subordinate spaces; pooling environmental samples obtained within each of the one or more subordinate locations or subordinate spaces; measuring an amount of the infectious agent in the pooled environmental samples and pooled biological samples for each of the one or more subordinate locations or subordinate spaces; assigning an risk score to each of the one or more subordinate locations or subordinate spaces based on the amount of infectious agent in the pooled environmental samples in a subordinate location or subordinate space as compared to each other subordinate location or subordinate space; and screening biological samples from subordinate locations or subordinate spaces that have a higher risk score before screening biological samples from subordinate locations or subordinate spaces that have a lower risk score.

The present disclosure provides methods for screening biological samples obtained from subjects at a subordinate location within a geographic region, or a subordinate space within the subordinate location for a biomarker by dividing the geographic region into one or more subordinate locations or dividing the subordinate locations into one or more subordinate spaces; pooling environmental samples obtained within each of the one or more subordinate locations or subordinate spaces; pooling biological samples obtained from subjects within each of the one or more subordinate locations or subordinate spaces; measuring an amount of the biomarker in the pooled environmental samples and pooled biological samples for each of the one or more subordinate locations or subordinate spaces; assigning an risk score to each of the one or more subordinate locations or subordinate spaces based on the amount of the biomarker in the pooled environmental samples and the pooled biological samples in a subordinate location or subordinate space as compared to each other subordinate location or subordinate space; and screening biological samples from subordinate locations or subordinate spaces that have a higher risk score before screening biological samples from subordinate locations or subordinate spaces that have a lower risk score.

The present disclosure provides methods for screening biological samples obtained from subjects at a subordinate location within a geographic region, or a subordinate space within the subordinate location for a biomarker by dividing the geographic region into one or more subordinate locations or dividing the subordinate locations into one or more subordinate spaces; pooling environmental samples obtained within each of the one or more subordinate locations or subordinate spaces; measuring an amount of the biomarker in the pooled environmental samples for each of the one or more subordinate locations or subordinate spaces; assigning an risk score to each of the one or more subordinate locations or subordinate spaces based on the amount of the biomarker in the pooled environmental samples in a subordinate location or subordinate space as compared to each other subordinate location or subordinate space; and screening biological samples from subordinate locations or subordinate spaces that have a higher risk score before screening biological samples from subordinate locations or subordinate spaces that have a lower risk score.

In some embodiments of each or any of the above- or below-mentioned embodiments, the infectious agent is a virus or a bacterium.

In some embodiments of each or any of the above- or below-mentioned embodiments, the virus is SARS-CoV-2.

In some embodiments of each or any of the above- or below-mentioned embodiments, the environmental sample is a bioaerosol.

In some embodiments of each or any of the above- or below-mentioned embodiments, the environmental and/or biological samples are geo-tagged.

In some embodiments of each or any of the above- or below-mentioned embodiments, the environmental and/or biological samples are barcoded.

In some embodiments of each or any of the above- or below-mentioned embodiments, the environmental and/or biological samples are pooled at a ratio of about 2:1 to about 10,000:1.

In some embodiments of each or any of the above- or below-mentioned embodiments, the environmental and/or biological samples are pooled at a ratio of about 2:1 to about 1,000:1.

In some embodiments of each or any of the above- or below-mentioned embodiments, the environmental and/or biological samples are pooled at a ratio of about 2:1 to about 100:1.

In some embodiments of each or any of the above- or below-mentioned embodiments, a subject is considered within a subregion if the subject resides, travels through, and/or works in the subregion.

In some embodiments of each or any of the above- or below-mentioned embodiments, the environmental and/or biological samples are analyzed by a high-throughput method.

In some embodiments of each or any of the above- or below-mentioned embodiments, the environmental and/or biological samples are analyzed by high-throughput PCR.

In some embodiments of each or any of the above- or below-mentioned embodiments, the one or more subordinate locations are adjacent to one another.

In some embodiments of each or any of the above- or below-mentioned embodiments, the geographic region is a country, state, county, city, or neighborhood.

In some embodiments of each or any of the above- or below-mentioned embodiments, the one or more subordinate locations include one or more counties, cities, or city blocks.

In some embodiments of each or any of the above- or below-mentioned embodiments, the one or more subordinate locations are a city block, multiple city blocks, a house(s) or a building(s).

In some embodiments of each or any of the above- or below-mentioned embodiments, the one or more subordinate locations are buildings associated with a specific type of business or trade.

In some embodiments of each or any of the above- or below-mentioned embodiments, the one or more subordinate locations are buildings having a common structural feature.

In some embodiments of each or any of the above- or below-mentioned embodiments, the one or more subordinate locations have a longitude and a latitude or other GPS coordinate scheme.

In some embodiments of each or any of the above- or below-mentioned embodiments, the environmental samples are air samples.

In some embodiments of each or any of the above- or below-mentioned embodiments, the environmental samples are from a dry or a wet surface.

In some embodiments of each or any of the above- or below-mentioned embodiments, the dry surface is a door handle, window, mirror, or other surface prone to condensation.

In some embodiments of each or any of the above- or below-mentioned embodiments, the environmental and/or biological samples are pooled from 2-1,000 subordinate locations or subordinate spaces.

In some embodiments of each or any of the above- or below-mentioned embodiments, the environmental and/or biological samples are pooled from 10-100 subordinate locations or subordinate spaces.

The present disclosure also provides methods for pooling biological and/or environmental samples at a subordinate location within a geographic region or a subordinate space within the subordinate location by a.) dividing the geographic region into one or more subordinate locations, or dividing the subordinate locations into one or more subordinate spaces; b.) pooling a first set of environmental samples obtained within each of the one or more subordinate locations or subordinate spaces and pooling a first set of biological samples obtained from subjects within each of the one or more subordinate locations or subordinate spaces; c.) measuring an amount of an infectious agent in the first set of pooled environmental samples and pooled biological samples for each of the one or more subordinate locations or subordinate spaces; d.) assigning a risk score to each of the one or more subordinate locations or subordinate spaces based on the amount of infectious agent in the first set of pooled environmental samples and/or the pooled biological samples in each subordinate location or subordinate space as compared to each other subordinate location or subordinate space; e.) pooling a second set of environmental samples and biological samples from the one or more subordinate locations or subordinate spaces, wherein the second set of environmental samples and biological samples are pooled at a higher ratio from subordinate locations or subordinate spaces assigned a lower risk score as compared to subordinate locations or subordinate spaces assigned a higher risk score; and f.) optionally repeating steps b. through e. to repeatedly update the risk score for each of the one or more subordinate locations or subordinate spaces.

The present disclosure also provides methods for pooling biological samples and/or environmental samples at a subordinate location within a geographic region or a subordinate space within the subordinate location by a.) dividing the geographic region into one or more subordinate locations, or dividing the subordinate locations into one or more subordinate spaces; b.) pooling a first set of environmental samples obtained within each of the one or more subordinate locations or subordinate spaces and pooling a first set of biological samples obtained from subjects within each of the one or more subordinate locations or subordinate spaces; c.) measuring an amount of a biomarker in the first set of pooled environmental samples and pooled biological samples for each of the one or more subordinate locations or subordinate spaces; d.) assigning a risk score to each of the one or more subordinate locations or subordinate spaces based on the amount of the biomarker in the first set of pooled environmental samples and the pooled biological samples in each subordinate location or subordinate space as compared to each other subordinate location or subordinate space; e.) pooling a second set of environmental samples and biological samples from the one or more subordinate locations or subordinate spaces, wherein the second set of environmental samples and biological samples are pooled at a higher ratio from subordinate locations or subordinate spaces assigned a lower risk score as compared to subordinate locations or subordinate spaces assigned a higher risk score; and f.) optionally repeating steps b. through e. to repeatedly update the risk score for each of the one or more subordinate locations or subordinate spaces.

In some embodiments of each or any of the above- or below-mentioned embodiments, the infectious agent is a virus or a bacterium.

In some embodiments of each or any of the above- or below-mentioned embodiments, the risk score is an infectious agent risk score.

In some embodiments of each or any of the above- or below-mentioned embodiments, the virus is SARS-CoV-2.

In some embodiments of each or any of the above- or below-mentioned embodiments, the geographic region is a country, state, county, city, or neighborhood.

In some embodiments of each or any of the above- or below-mentioned embodiments, the geographic region is a state.

In some embodiments of each or any of the above- or below-mentioned embodiments, the geographic region is a city.

In some embodiments of each or any of the above- or below-mentioned embodiments, the one or more subordinate locations include one or more counties, cities, or city blocks.

In some embodiments of each or any of the above- or below-mentioned embodiments, the first and the second set of environmental samples includes a bioaerosol.

In some embodiments of each or any of the above- or below-mentioned embodiments, the methods further comprise screening biological samples from subordinate locations that have a higher infectious agent risk score before screening biological samples from subordinate locations that have a lower infectious agent risk score.

In some embodiments of each or any of the above- or below-mentioned embodiments, the one or more subordinate locations are scored on a scale of 1 to 10 with a score of 1 corresponding to a low infectious agent risk score and a score of 10 corresponding to a high infectious agent risk score.

In some embodiments of each or any of the above- or below-mentioned embodiments, the one or more subordinate locations are scored from low, medium, or high with a score of low corresponding to a low infectious agent risk score and a score of high corresponding to a high infectious agent risk score.

In some embodiments of each or any of the above- or below-mentioned embodiments, the first and the second set of environmental and/or biological samples are re-prioritized, re-aggregated, and/or discarded based on the infectious agent risk score from the subregion from which the samples were obtained.

In some embodiments of each or any of the above- or below-mentioned embodiments, the first set and the second set of environmental and/or biological samples are geo-tagged.

In some embodiments of each or any of the above- or below-mentioned embodiments, the first set and the second set of environmental and/or biological samples are bar-coded.

In some embodiments of each or any of the above- or below-mentioned embodiments, the first set and the second set of environmental and/or biological samples are pooled at a ratio of about 2:1 to about 10,000:1.

In some embodiments of each or any of the above- or below-mentioned embodiments, the first set and the second set of environmental and/or biological samples are pooled at a ratio of about 2:1 to about 1,000:1.

In some embodiments of each or any of the above- or below-mentioned embodiments, the first set and the second set of environmental and/or biological samples are pooled at a ratio of about 2:1 to about 100:1.

In some embodiments of each or any of the above- or below-mentioned embodiments, the subjects are considered within a subregion where they reside, travel through, and/or work in the subregion.

In some embodiments of each or any of the above- or below-mentioned embodiments, the first set and the second set of environmental and/or biological samples are analyzed by a high-throughput method.

In some embodiments of each or any of the above- or below-mentioned embodiments, the first set and the second set of environmental and/or biological samples are analyzed by high-throughput PCR.

In some embodiments of each or any of the above- or below-mentioned embodiments, the one or more subordinate locations are adjacent to one another.

In some embodiments of each or any of the above- or below-mentioned embodiments, the one or more subordinate locations are a city block, multiple city blocks, a house(s), or a building(s).

In some embodiments of each or any of the above- or below-mentioned embodiments, the one or more subordinate locations are buildings associated with a specific business or trade.

In some embodiments of each or any of the above- or below-mentioned embodiments, the one or more subordinate locations are buildings having a common structural feature.

In some embodiments of each or any of the above- or below-mentioned embodiments, the one or more subordinate locations have a longitude and a latitude or other GPS coordinate scheme.

In some embodiments of each or any of the above- or below-mentioned embodiments, the first and second set of environmental samples are air samples.

In some embodiments of each or any of the above- or below-mentioned embodiments, the first and second set of environmental sample are from a dry or a wet surface.

In some embodiments of each or any of the above- or below-mentioned embodiments, the dry surface is a door handle, window, mirror, or other surface prone to condensation.

In some embodiments of each or any of the above- or below-mentioned embodiments, the first and second set of environmental and/or biological samples are pooled from 1-1,000 subordinate locations.

In some embodiments of each or any of the above- or below-mentioned embodiments, the first and second set of environmental and/or biological samples are pooled from 10-100 subordinate locations.

The present disclosure also provides methods of determining a risk of an infection from an infectious agent (e.g., virus) for a subject in a subordinate location of a geographic region or a subordinate space of the subordinate location by generating a heat map of the amount of infectious agent (and/or number of subjects infected with the infectious agent) in the one or more subordinate locations or subordinate spaces, wherein the heat map is generated by: pooling environmental samples and biological samples obtained within each of the one or more subordinate locations or subordinate spaces; measuring an amount of infectious agent in the pooled environmental samples and pooled biological samples for each of the one or more subordinate locations or subordinate spaces, and assigning each of the one or more subordinate locations or subordinate spaces a risk score based on the amount of infectious agent in the pooled environmental samples and the pooled biological samples in each of the one or more subordinate locations or subordinate spaces as compared to each other subordinate location or subordinate space; and determining the risk of infection for the subject based on the risk score assigned to the subordinate location or subordinate space of the individual.

The present disclosure also provides methods of determining a risk of an infection from an infectious agent (e.g., virus) for a subject in a subordinate location of a geographic region or a subordinate space of the subordinate location by generating a heat map of the amount of a biomarker and/or number of subjects having the biomarker at one or more subordinate locations or subordinate spaces, wherein the heat map is generated by: pooling environmental samples and biological samples obtained within each of the one or more subordinate locations or subordinate spaces; measuring an amount of biomarker in the pooled environmental samples and pooled biological samples for each of the one or more subordinate locations or subordinate spaces, and assigning each of the one or more subordinate locations or subordinate spaces a risk score based on the amount of biomarker in the pooled environmental samples and the pooled biological samples in each of the one or more subordinate locations or subordinate spaces as compared to each other subordinate location or subordinate space; and determining the risk of infection for the subject based on the risk score assigned to the subordinate location or subordinate space of the individual.

The present disclosure also provides methods of determining a risk of a viral infection for a subject in a subordinate location of a geographic region or a subordinate space in the subordinate location, by generating a heat map of the amount of virus and/or number of subjects infected with the virus at one or more subordinate locations or subordinate spaces, wherein the heat map is generated by: pooling environmental samples and biological samples obtained within each of the one or more subordinate locations or subordinate spaces; measuring an amount of virus in the pooled environmental samples and pooled biological samples for each of the one or more subordinate locations or subordinate spaces, and assigning each of the one or more subordinate locations or subordinate spaces a risk score based on the amount of virus in the pooled environmental samples and the pooled biological samples in each of the one or more subordinate locations or subordinate spaces as compared to each other subordinate location or subordinate space; and determining the risk of viral infection for the subject based on the risk score assigned to the subordinate location or subordinate space of the individual.

In some embodiments of each or any of the above- or below-mentioned embodiments, the methods further comprise clearing or re-opening one or more subordinate locations or subordinate spaces based on the risk score. In another embodiment, the methods further comprise clearing or re-opening one or more subordinate locations or subordinate spaces based on the risk score or otherwise declaring the subordinate locations or subordinate spaces negative or presumptive negative.

In some embodiments of each or any of the above- or below-mentioned embodiments, the virus is SARS-CoV-2.

In some embodiments of each or any of the above- or below-mentioned embodiments, the geographic region is a country, state, county, city, or neighborhood.

In some embodiments of each or any of the above- or below-mentioned embodiments, the geographic region is a city.

In some embodiments of each or any of the above- or below-mentioned embodiments, the one or more subordinate locations include one or more counties, cities, or city blocks.

In some embodiments of each or any of the above- or below-mentioned embodiments, the environmental sample includes a bioaerosol.

In some embodiments of each or any of the above- or below-mentioned embodiments, the subject has not previously been infected with the virus.

In some embodiments of each or any of the above- or below-mentioned embodiments, the methods further comprise screening biological samples from a subregion that has a higher risk score before screening biological samples from a subregion that has a lower risk score.

In some embodiments of each or any of the above- or below-mentioned embodiments, a geographic region is scored on a scale of 1 to 10 with a score of 1 corresponding to a low risk score and a score of 10 corresponding to a high risk score.

In some embodiments of each or any of the above- or below-mentioned embodiments, the pooling ratio is higher for geographic regions with a lower viral infection score than geographic region having a higher risk score.

In some embodiments of each or any of the above- or below-mentioned embodiments, the environmental and/or biological samples are re-prioritized, re-aggregated, and/or discarded based on the risk score from the subregion from which they were obtained.

In some embodiments of each or any of the above- or below-mentioned embodiments, the environmental and/or biological samples are geo-tagged.

In some embodiments of each or any of the above- or below-mentioned embodiments, the environmental and/or biological samples are barcoded.

In some embodiments of each or any of the above- or below-mentioned embodiments, the environmental and/or biological samples are pooled at a ratio of about 2:1 to about 10,000:1.

In some embodiments of each or any of the above- or below-mentioned embodiments, the environmental and/or biological samples are pooled at a ratio of about 2:1 to about 1,000:1.

In some embodiments of each or any of the above- or below-mentioned embodiments, the environmental and/or biological samples are pooled at a ratio of about 2:1 to about 100:1.

In some embodiments of each or any of the above- or below-mentioned embodiments, a subject is considered in a subregion if the subject resides, travels through, and/or works in the subregion.

In some embodiments of each or any of the above- or below-mentioned embodiments, the environmental and/or biological samples are analyzed by a high-throughput method.

In some embodiments of each or any of the above- or below-mentioned embodiments, the environmental and/or biological samples are analyzed by high-throughput PCR.

In some embodiments of each or any of the above- or below-mentioned embodiments, the one or more subordinate locations are adjacent to one another.

In some embodiments of each or any of the above- or below-mentioned embodiments, the one or more subordinate locations are not adjacent to one another.

In some embodiments of each or any of the above- or below-mentioned embodiments, the one or more subordinate locations are buildings associated with a certain a business or trade.

In some embodiments of each or any of the above- or below-mentioned embodiments, the one or more subordinate locations are buildings having a common structural feature.

In some embodiments of each or any of the above- or below-mentioned embodiments, the one or more subordinate locations have a longitude and a latitude or other GPS coordinate scheme.

In some embodiments of each or any of the above- or below-mentioned embodiments, the environmental samples are air samples.

In some embodiments of each or any of the above- or below-mentioned embodiments, the environmental sample are from a dry or a wet surface.

In some embodiments of each or any of the above- or below-mentioned embodiments, the dry surface is a door handle, window, mirror, or other surface prone to condensation.

In some embodiments of each or any of the above- or below-mentioned embodiments, environmental and/or biological samples are pooled from 1-1,000 subordinate locations or subordinate spaces.

In some embodiments of each or any of the above- or below-mentioned embodiments, environmental and/or biological samples are pooled from 10-100 subordinate locations or subordinate spaces.

The present disclosure also provides methods of screening biological samples obtained from subjects at one or more subordinate locations in a geographic region or one or more subordinate spaces in the subordinate location, by determining a number of subjects infected with a virus at the one or more subordinate locations or subordinate spaces to generate a first heat-map based on a risk score for the one or more subordinate locations or subordinate spaces; generating a second heat map of an amount of virus in each of the one or more subordinate locations or subordinate spaces wherein the heat map is generated by: pooling environmental samples and biological samples obtained within each of the one or more subordinate locations or subordinate spaces; measuring an amount of virus in the pooled environmental samples and pooled biological samples for each of the one or more subordinate locations or subordinate spaces, and assigning each of the one or more subordinate locations or subordinate spaces a second risk score based on the amount of virus in the pooled environmental samples and the pooled biological samples in each subordinate location or subordinate space as compared to each other subordinate location or subordinate space; and comparing the first heat map to the second heat map; identifying changes between the risk score in the one or more subordinate locations or subordinate spaces between the first heat map and the second heat map; and changing a screening protocol in any subordinate locations or subordinate spaces in which the risk score is different between the first heat map and the second heat map.

The present disclosure also provides methods of screening biological samples obtained from subjects at one or more subordinate locations in a geographic region or one or more subordinate spaces in the subordinate location, by determining a number of subjects with a biomarker at the one or more subordinate locations or subordinate spaces to generate a first heat-map based on a risk score for the one or more subordinate locations or subordinate spaces; generating a second heat map of an amount of the biomarker in each of the one or more subordinate locations or subordinate spaces wherein the heat map is generated by: pooling environmental samples and biological samples obtained within each of the one or more subordinate locations or subordinate spaces; measuring an amount of the biomarker in the pooled environmental samples and pooled biological samples for each of the one or more subordinate locations or subordinate spaces, and assigning each of the one or more subordinate locations or subordinate spaces a second risk score based on the amount of the biomarker in the pooled environmental samples and the pooled biological samples in each subordinate location or subordinate space as compared to each other subordinate location or subordinate space; and comparing the first heat map to the second heat map; identifying changes between the risk score in the one or more subordinate locations or subordinate spaces between the first heat map and the second heat map; and changing a screening protocol in any subordinate locations or subordinate spaces in which the risk score is different between the first heat map and the second heat map.

The present disclosure also provides methods of screening biological samples obtained from subjects at one or more subordinate locations within a geographic region or subordinate spaces within the subordinate location, by a.) generating a first heat map of an amount of virus in each of a first group one or more subordinate locations or subordinate space wherein the heat map is generated by: pooling a first set of environmental samples and biological samples obtained within each of the one or more subordinate locations or subordinate space in the first group; measuring an amount of virus in the first set of pooled environmental samples and pooled biological samples for each of the one or more subordinate locations or subordinate space in the first group, and assigning each of the one or more subordinate locations or subordinate space in the first group a first risk score based on the amount of virus in the first set of pooled environmental samples and the pooled biological samples in each subordinate location or subordinate space in the first group as compared to each other subordinate location or subordinate space in the first group; and b.) generating a second heat map of an amount of virus in each of a second group of one or more subordinate locations or subordinate spaces wherein the heat map is generated by: pooling a second set of environmental samples and biological samples obtained within each of the one or more subordinate locations or subordinate spaces in the second group;

measuring an amount of virus in the second set of pooled environmental samples and pooled biological samples for each of the one or more subordinate locations or subordinate spaces in the second group, and assigning each of the one or more subordinate locations or subordinate spaces in the second group a second risk score based on the amount of virus in the pooled environmental samples and the pooled biological samples in each subordinate location or subordinate space in the second group as compared to each other subordinate location or subordinate space in the second group; and c.) comparing the first heat map to the second heat map; d.) identifying changes in the risk score in the one or more subordinate locations or subordinate spaces between the first heat map and the second heat map; e.) changing a screening protocol in any subordinate locations or subordinate spaces in which the risk score is different between the first heat map and the second heat map; and f.) optionally repeating steps a. through e.

The present disclosure also provides methods of screening biological samples obtained from subjects at one or more subordinate locations within a geographic region or subordinate spaces within the subordinate location, by a.) generating a first heat map of an amount of a biomarker in each of a first group one or more subordinate locations or subordinate space wherein the heat map is generated by: pooling a first set of environmental samples and biological samples obtained within each of the one or more subordinate locations or subordinate space in the first group; measuring an amount of the biomarker in the first set of pooled environmental samples and pooled biological samples for each of the one or more subordinate locations or subordinate space in the first group, and assigning each of the one or more subordinate locations or subordinate spaces in the first group a first risk score based on the amount of the biomarker in the first set of pooled environmental samples and the pooled biological samples in each subordinate location or subordinate space in the first group as compared to each other subordinate location or subordinate space in the first group; and b.) generating a second heat map of an amount of the biomarker in each of a second group of one or more subordinate locations or subordinate spaces wherein the heat map is generated by: pooling a second set of environmental samples and biological samples obtained within each of the one or more subordinate locations or subordinate spaces in the second group; measuring an amount of the biomarker in the second set of pooled environmental samples and pooled biological samples for each of the one or more subordinate locations or subordinate spaces in the second group, and assigning each of the one or more subordinate locations or subordinate spaces in the second group a second risk score based on the amount of the biomarker in the pooled environmental samples and the pooled biological samples in each subordinate location or subordinate space in the second group as compared to each other subordinate location or subordinate space in the second group; and c.) comparing the first heat map to the second heat map; d.) identifying changes in the risk score in the one or more subordinate locations or subordinate spaces between the first heat map and the second heat map; e.) changing a screening protocol in any subordinate locations or subordinate spaces in which the risk score is different between the first heat map and the second heat map; and f.) optionally repeating steps a. through e.

In some embodiments of each or any of the above- or below-mentioned embodiments, the virus is SARS-CoV-2.

The present disclosure also provides a heat map generated by the methods disclosed herein.

In some embodiments of each or any of the above- or below-mentioned embodiments, the change in the screening protocol includes prioritizing for screening biological samples from subordinate locations or subordinate spaces assigned a higher risk score over biological samples from subordinate locations or subordinate spaces assigned a lower risk score.

In some embodiments of each or any of the above- or below-mentioned embodiments, the change in the screening protocol includes revising the risk score of other biological samples already in a screening process.

In some embodiments of each or any of the above- or below-mentioned embodiments, the change in the screening protocol includes discarding samples.

The present disclosure also provides methods for reducing costs associated with screening a population of subjects for a viral infection in a geographic region, by dividing a geographic region into a first group of one or more subordinate locations or dividing the one or more subordinate locations into one or more subordinate spaces; pooling a first set of environmental samples and biological samples obtained from the first group of one or more subordinate locations or subordinate spaces; measuring an amount of virus in the first set of pooled environmental samples and pooled biological samples for each of the first group of one or more subordinate locations or subordinate spaces; assigning a risk score to each of the first group of one or more subordinate locations or subordinate spaces based on the amount of virus in the first set of pooled environmental samples and biological samples in each subordinate location or subordinate space in the first group as compared to each other subordinate location or subordinate space in the first group; and pooling a second set of environmental samples and biological samples from a second group of one or more subordinate locations or subordinate spaces in the geographic region, wherein samples are pooled at a higher ratio from subordinate locations or subordinate spaces in the first group assigned a low risk score versus subordinate locations or subordinate spaces identified as having a higher risk score, wherein pooling the environmental samples and biological samples reduces costs associated with screening the population of subjects.

In some embodiments of each or any of the above- or below-mentioned embodiments, the virus is SARS-CoV-2.

In some embodiments of each or any of the above- or below-mentioned embodiments, the first group of one or more subordinate locations or subordinate spaces is the same as the second group of one or more subordinate locations or subordinate spaces.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
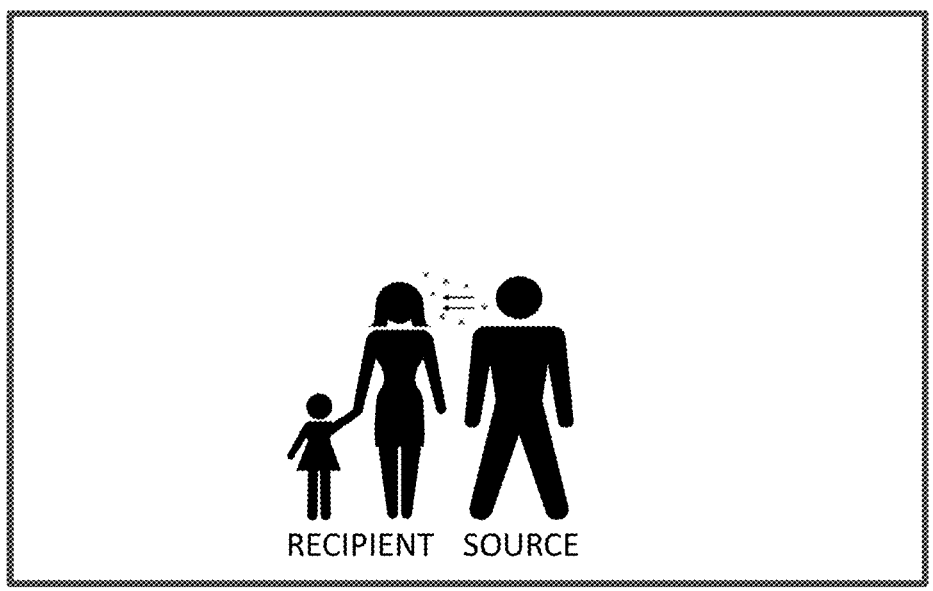
FIG. 1 shows transmission of an infectious agent from a source in close proximity to a recipient by the source discharging (exhaling, coughing, etc.) the infectious agent into air breathed in by the recipient.
Figure 2:
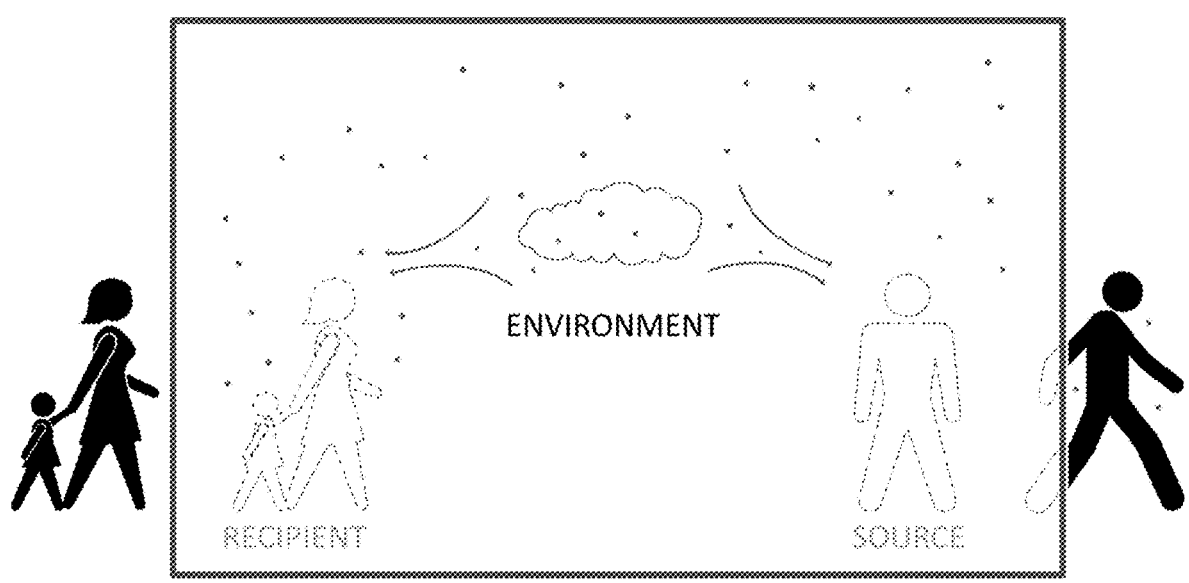
FIG. 2 shows an infectious agent remaining in the environment (e.g., air) well after a source has departed a location where the infectious agent was discharged (exhaling, coughing, etc.).
Figure 3:
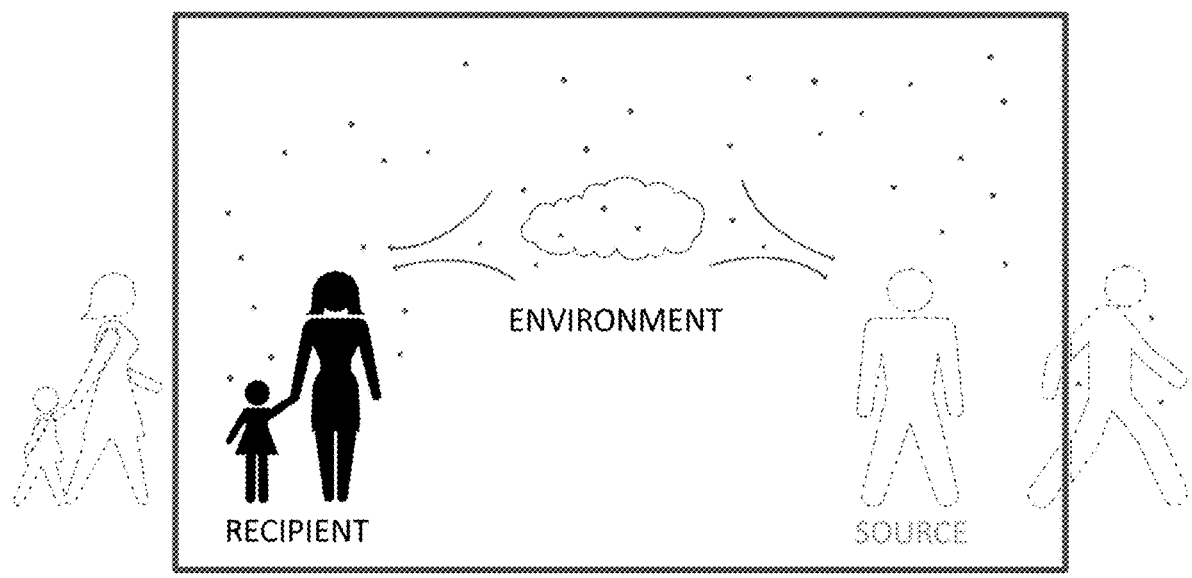
FIG. 3 shows exposure of a recipient to an environment that contains an infectious agent (e.g., the environment becomes the infectious source) but does not contain any subjects infected with the agent.
Figure 4:
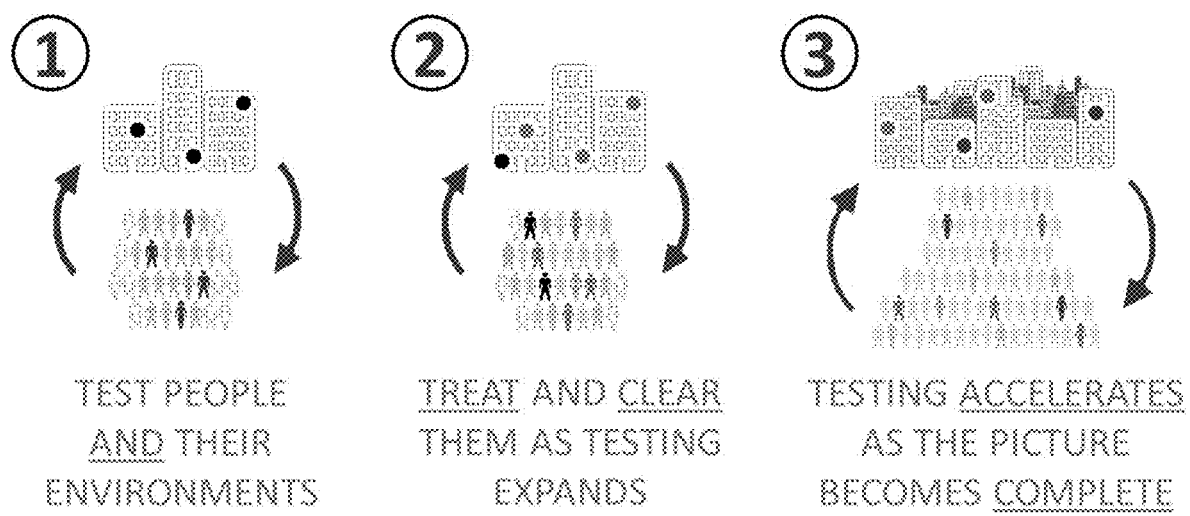
FIG. 4 depicts an exemplary embodiment of the screening methods disclosed herein. As shown in panel 1, people and environments at a number of subordinate spaces (i.e., rooms within a number of buildings) are tested for the presence (and amount) of infectious agent. Information on the amount of the infectious agent within the subordinate spaces is used to generate a heat map that displays those locations that are hotter (i.e., have a larger quantity of infectious agent) than other locations. In panel 2, people in the spaces that are found to have the infectious agent are treated and/or cleared (shown as the change from a black dot to a grey dot between panel 1 and 2) all while samples are pooled at a higher ratio in spaces identified by the heat map as having a higher amount of infectious agent as compared to spaces identified on the heat map as having a relatively lower amount of the infectious agent. In panel 3, testing accelerates and expands to further spaces as samples from people and the environment presumed to be positive by the heat map are prioritized for analysis and samples presumed to be negative by the heat map are pooled at higher ratios allowing for the testing of additional spaces.

In the case of a highly contagious airborne pathogen such as SARS-CoV-2, an subject may shed (e.g., exhale) virus particles into the air which remain aloft minutes or hours thereafter, infecting persons who never physically encountered the subject in-person (see, e.g., FIGS. 1-3). Infectious virons may also be transported through HVAC or tidal air movements to other areas within a space or building. Further still, a person is contagious generally 1-3 days before onset of symptoms, making behavioral preventive measures, contact tracing, and isolation nearly impossible. Complicating matters further still, there is often a shortage of resources for testing subjects for an infectious agent such as a virus.

The methods disclosed herein employ sample pooling techniques to mitigate the need to test every subject in a geographic region, a subordinate location within the geographic region, or a subordinate space within the subordinate location for the infectious agent. Advantageously, such methods may reduce the time, resources, and ultimately cost of testing for the infectious agent.

The methods disclosed herein may also be used to reduce a death rate due to the infectious agent in the geographic region, subordinate location, and/or subordinate space.

Additionally, the methods disclosed herein may be used to clear one or more subordinate locations or subordinate spaces in a geographic region (e.g., identify one or more subordinate locations or subordinate spaces as low-risk for exposure to the infectious agent).

The methods disclosed herein may be used to monitor the presence, movement, and/or mutation of infectious agents.

Furthermore, the methods disclosed herein may be used to monitor relative levels of distinct strains of an infectious agent such as a coronavirus or influenza.

Moreover, the methods disclosed herein may be used to continuously surveil a geographic region, a subordinate location, or a subordinate space for an infectious agent. In some embodiments, a geographic region, a subordinate location, or a subordinate space may not have the infectious agent or subjects within the geographic region, subordinate location, or subordinate space exhibit no symptoms of the infectious agent, but the methods disclosed herein are nonetheless employed so that any occurrence of the infectious agent can be spotted early on and mitigated. Advantageously, where the infectious agent is detected in a geographic region, a subordinate location, or a subordinate space (e.g., detected in environmental samples or biological samples collected from such geographic region, subordinate location, or subordinate space) but subjects in the geographic region, subordinate location, or subordinate space do not exhibit symptoms of the infectious agent, the subjects may be screened to identify biomarkers of resistance to the infectious agent such as genetic markers or blood-based biomarkers. Such subjects may be purposefully excluded from the screening methods.

The methods disclosed herein may also be used to identify a subject's risk of infection by an infectious agent including, subjects that have already been infected with the infectious agent such as subjects diagnosed as infected with the infectious agent or subject that have antibodies to the infectious agent. For example, a subject that resides in a subordinate location that has a high amount of the infectious agent may be considered to have a low risk of infection where that subject has antibodies to the agent in his or her blood.

The methods disclosed herein may be used to generate a heat map such as an environmental and/or clinical heat map for an infectious agent including, a communicable infectious agent (e.g., a data visualization that shows a magnitude/amount of an infectious agent as color in two dimensions versus subordinate locations or subordinate spaces from which environmental and/or clinical sample were obtained).

A heat map may include a data set in addition to the amount of the infectious agent (or may be filtered to contain and/or display the amount of infectious agent for a particular data set). For example, a heat map may include data pertaining to an individual's (i.e., a subject from which a biological sample(s) is obtained) occupation, social or an ethnic demographic, and/or social meta-data, etc. The heat may also pull data pertaining to the subordinate location or subordinate space from which the environmental samples are obtained including, for example, a type of building or structure (e.g., single-family home, multiple-unit dwelling, low-rise, high-rise, building with a particular HVAC or ventilation system, etc.), the type of business from which the sample is obtained (e.g., an financial services company, a restaurant, a grocery store, etc.), patient meta-data, results of an interview of the subject (e.g., human or software based), or subject specific medical data from health care information systems. The heat map may include such data or be filtered to output information relevant to the infectious agent for one or more of the data sets. For example, environmental and/or biological samples may be obtained from a subordinate location within a geographic region (or a subordinate space within the subordinate location) associated with a certain type of business and certain subjects associated with the business (e.g., the samples may be obtained from a hospital and the workers at the hospital). The heat map may include (or may be filtered to contain and/or display the amount of infectious agent for a particular data set) such as cell phone data, social media data, CDC data, hospital data, nursing home data, long-term care facility data, government data, etc.

The heat map and/or testing/screening facility for the environmental and/or biological samples may be linked to one another and may optionally be linked to other systems used to test and/screen a geographic region, a subordinate location, or a subordinate space for the infectious agent.

The heat map may also include the amount of infectious agent collected from environmental and/or biological samples from a low-income neighborhood and/or a high-income neighborhood. The environmental and/or biological samples may also be obtained from subjects deemed essential workers (e.g., hospital workers, first responders, and/or grocery store workers, etc.) and/or the places in which they live and/or work.

The heat map may factor in an individual's movement history including through sparsely populated areas and densely populated areas, or through certain subordinate locations and/or spaces. Biological samples obtained from the subject may be included or excluded from the data set for the heat map. For example, a heat map may include a set of data from environmental samples and/or biological samples but may exclude biological sample(s) from an infected subject that travels though sparsely populated areas.

The heat may also include data regarding transmission pathways, occupational profiles, airflow patterns, and/or vector organisms (e.g. human, avian, rodent, or arthropods).

The methods may also be used to generate a heat map based on detection of one or more biomarkers that may indicate an immuno-response to an infectious agent, a predisposition to infection with an infectious agent, tolerance to the infectious agent, or likely responsiveness to prophylactic treatments or therapeutic interventions for the infectious agent. The biomarker may also indicate a risk of death or morbidity from the infectious agent.

The heat maps disclosed herein may be geospatial and contain information about the magnitude/amount of an infectious agent in a living or work space. The heat maps may provide an exposure profile for an infectious agent (e.g., occupational or other behavioral parameter or group of parameters, etc.). The heat maps may also provide an exposure pathway for an infectious agent (e.g., HVAC, or tidal airflow, etc.). The heat maps disclosed herein may be used to guide quarantining or stay-at-home orders. Additionally, the heat maps may be used to clear subregion determined to be of a low risk of infection from an infectious agent.

The present disclosure provides methods for screening biological samples obtained from subjects at a geographic region for an infectious agent (e.g., SARS-CoV-2). Such methods may include dividing the geographic region into one or more subordinate locations; pooling environmental samples obtained within each of the one or more subordinate locations; pooling biological samples obtained from subjects within each of the one or more subordinate locations; measuring an amount of the infectious agent in the pooled environmental samples and pooled biological samples for each of the one or more subordinate locations; assigning a risk score to each of the one or more subordinate locations based on the amount of infectious agent in the pooled environmental samples and the pooled biological samples in a subordinate location as compared to each other subordinate location; and screening biological samples from subordinate location that have a higher risk score before screening biological samples from subordinate locations that have a lower risk score.

The present disclosure provides methods for screening biological samples obtained from subjects at a geographic region for an infectious agent (e.g., SARS-CoV-2). Such methods may include dividing one or more subordinate locations in one or more subordinate spaces; pooling environmental samples obtained within each of the one or more subordinate spaces; pooling biological samples obtained from subjects within each of the one or more subordinate spaces; measuring an amount of the infectious agent in the pooled environmental samples and pooled biological samples for each of the one or more subordinate spaces; assigning a risk score to each of the one or more subordinate spaces based on the amount of infectious agent in the pooled environmental samples and the pooled biological samples in a subordinate space as compared to each other subordinate space; and screening biological samples from subordinate spaces that have a higher risk score before screening biological samples from subordinate spaces that have a lower risk score.

Additionally, the present disclosure also provides methods for pooling biological samples obtained from subjects at a geographic region. Such methods may include a.) dividing the geographic region into one or more subordinate locations; b.) pooling a first set of environmental samples obtained within each of the one or more subordinate locations and pooling a first set of biological samples obtained from subjects within each of the one or more subordinate locations; c.) measuring an amount of an infectious agent (e.g., SARS-CoV-2) in the first set of pooled environmental samples and pooled biological samples for each of the one or more subordinate locations; d.) assigning a risk score to each of the one or more subordinate locations based on the amount of infectious agent in the first set of pooled environmental samples and the pooled biological samples in each subordinate location as compared to each other subordinate location; e.) pooling a second set of environmental samples and biological samples from the one or more subordinate locations, wherein the second set of environmental samples and biological samples are pooled at a higher ratio from subordinate locations assigned a lower risk score as compared to subordinate locations assigned a higher risk score; and f.) optionally repeating steps b. through e. to repeatedly update the risk score for each of the one or more subordinate locations.

Additionally, the present disclosure also provides methods for pooling biological samples obtained from subjects at a geographic region. Such methods may include a.) dividing a subordinate location into one or more subordinate spaces; b.) pooling a first set of environmental samples obtained within each of the one or more subordinate spaces and pooling a first set of biological samples obtained from subjects within each of the one or more subordinate spaces; c.) measuring an amount of an infectious agent (e.g., SARS-CoV-2) in the first set of pooled environmental samples and pooled biological samples for each of the one or more subordinate spaces; d.) assigning a risk score to each of the one or more subordinate spaces based on the amount of infectious agent in the first set of pooled environmental samples and the pooled biological samples in each subordinate space as compared to each other subordinate space; e.) pooling a second set of environmental samples and biological samples from the one or more subordinate spaces, wherein the second set of environmental samples and biological samples are pooled at a higher ratio from subordinate spaces assigned a lower risk score as compared to subordinate spaces assigned a higher risk score; and f.) optionally repeating steps b. through e. to repeatedly update the risk score for each of the one or more subordinate spaces.

Furthermore, the present disclosure also provides methods of determining a risk of a viral infection (e.g., a SARS-CoV-2 infection) for a subject in a subordinate location of a geographic region (e.g., a subject that resides, travels through, and/or works in the subordinate location). Such methods may include generating a heat map of the amount of virus and/or number of subjects infected with the virus at one or more subordinate locations within the geographic region, wherein the heat map is generated by: pooling environmental samples and biological samples obtained within each of the one or more subordinate locations; measuring an amount of virus in the pooled environmental samples and pooled biological samples for each of the one or more subordinate locations, and assigning each of the one or more subordinate locations a risk score based on the amount of virus in the pooled environmental samples and the pooled biological samples in each of the one or more subordinate locations as compared to each other subordinate location; and determining the risk of viral infection for the subject based on the risk score assigned to the subordinate location of the individual. In an embodiment, the risk score assigned to the subject may be increased or decreased based on other factors including the subject's age, weight, ethnicity, and/or the presence or absence of a biomarker in the subject.

Moreover, the present disclosure also provides methods of screening biological samples obtained from subjects at one or more subordinate locations within a geographic region. Such methods may include determining a number of subjects infected with a virus (e.g., SARS-CoV-2) at the one or more subordinate locations to generate a first heat-map based on a risk score for the one or more subordinate locations; generating a second heat map of an amount of virus in each of the one or more subordinate locations wherein the heat map is generated by: pooling environmental samples and biological samples obtained within each of the one or more subordinate locations; measuring an amount of virus in the pooled environmental samples and pooled biological samples for each of the one or more subordinate locations, and assigning each of the one or more subordinate locations a second risk score based on the amount of virus in the pooled environmental samples and the pooled biological samples in each subordinate location as compared to each other subordinate location; and comparing the first heat map to the second heat map; identifying changes in the risk score in the one or more subordinate locations between the first heat map and the second heat map; and changing a screening protocol in any subordinate locations in which the risk score is different between the first heat map and the second heat map.

Additionally, the present disclosure also provides methods of screening biological samples obtained from subjects at one or more subordinate locations within a geographic region. Such methods may include a.) generating a first heat map of an amount of virus (e.g., SARS-CoV-2) in each of a first group one or more subordinate locations wherein the heat map is generated by: pooling a first set of environmental samples and biological samples obtained within each of the one or more subordinate locations in the first group; measuring an amount of virus in the first set of pooled environmental samples and pooled biological samples for each of the one or more subordinate locations in the first group, and assigning each of the one or more subordinate locations in the first group a first risk score based on the amount of virus in the first set of pooled environmental samples and the pooled biological samples in each subordinate location in the first group as compared to each other subordinate location in the first group; and b.) generating a second heat map of an amount of virus in each of a second group of one or more subordinate locations wherein the heat map is generated by: pooling a second set of environmental samples and biological samples obtained within each of the one or more subordinate locations in the second group; measuring an amount of virus in the second set of pooled environmental samples and pooled biological samples for each of the one or more subordinate locations in the second group, and assigning each of the one or more subordinate locations in the second group a second risk score based on the amount of virus in the pooled environmental samples and the pooled biological samples in each subordinate location in the second group as compared to each other subordinate location in the second group; c.) comparing the first heat map to the second heat map; d.) identifying changes in the risk score in the one or more subordinate locations between the first heat map and the second heat map; e.) changing a screening protocol in any subordinate locations in which the risk score is different between the first heat map and the second heat map; and f.) optionally repeating steps a. through e.

The change in the screening protocol may include prioritizing screening biological samples from subordinate locations or subordinate spaces assigned a higher risk score over biological samples from sub assigned a lower risk score, revising the risk score of other biological samples already in a screening process, and/or changing the screening protocol including discarding samples.

The present disclosure also provides methods for reducing costs associated with screening a population of subjects for a viral infection (e.g., a SARS-CoV-2 infection) in a geographic region. Such methods may include dividing the geographic region into a first group of one or more subordinate locations; pooling a first set of environmental samples and biological samples obtained from the first group of one or more subordinate locations; measuring an amount of virus in the first set of pooled environmental samples and pooled biological samples for each of the first group of one or more subordinate locations; assigning a risk score to each of the first group of one or more subordinate locations based on the amount of virus in the first set of pooled environmental samples and biological samples in each subordinate location in the first group as compared to each other subordinate location in the first group; and pooling a second set of environmental samples and biological samples from a second group of one or more subordinate locations in the geographic region, wherein samples are pooled at a higher ratio from subordinate locations in the first group assigned a low risk score versus subordinate locations identified as having a higher risk score, wherein pooling the environmental samples and biological samples reduces costs associated with screening the population of subjects.

The geographic region may be a country, state, county, city, or neighborhood. The geographic region may also be one or more countries (e.g., the European Union), states (e.g., Northeast U.S. states), counties, cities, or neighborhoods. In an embodiment, the geographic region is a state and buildings or subordinate locations and/or subordinate spaces therein.

The one or more subordinate locations in a geographic region may include one or more counties, cities, a city block(s), a house(s), or a building(s). In an embodiment, the one or more subordinate locations are buildings associated with a specific type of business or trade. In another embodiment, the one or more subordinate locations are buildings having a common structural feature. In another embodiment, the one or more subordinate locations are adjacent to one another. The subordinate locations or subordinate spaces may be a mode of transportation in the geographic region such as planes, buses, subways, train cars, Ubers/Lifts, taxis, cruise ships, etc. For example, the geographic region may be the United States and the subordinate locations may be all planes that fly in the United States or planes belonging to one or more airline carriers.

The subordinate locations or subordinate spaces may include a housing complex, a travel/transportation corridor, a specific building, a portion of a building (e.g., entrance and or alcove), a city block where homeless tend to aggregate, or isolated spots where homeless make camp, and/or a long-term care facility.

The methods may comprise screening biological samples and/or environmental samples from subordinate locations or subordinate spaces that have a higher risk score before screening biological samples and/or environmental samples from subordinate locations or subordinate spaces that have a lower risk score. A risk score may be based on the amount of infectious agent in the subordinate location or subordinate space. For example, a subordinate location or subordinate space with more infectious agent than another subordinate location or subordinate space has a higher risk score than the other subordinate location or subordinate space.

In an embodiment, the one or more subordinate locations or subordinate spaces are scored on a scale of one (1) to ten (10) with a score of one (1) corresponding to a low risk score and a score of ten (10) corresponding to a high risk score. In another embodiment, the one or more subordinate locations or subordinate spaces are scored from low, medium, or high with a score of low corresponding to a low risk score and a score of high corresponding to a high risk score. A higher risk score is associated with an increased risk of infection from the infectious agent versus a lower risk score.

In an embodiment, the first set of environmental and biological samples are obtained from the same number of sources for each of the subordinate locations and/or subordinate spaces (e.g., the number of environmental and/or biological samples for each of the locations and spaces is the same).

The second set of environmental samples and biological samples are pooled at a ratio of about 2:1 to about 10000:1 as compared to a pooling ratio for the first set of environmental samples and biological samples. For example, the second set of environmental samples and biological samples may be pooled at a ratio of 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1. 81:1, 82:1, 83:1, 84:1, 85:1, 86:1, 87:1, 88:1, 89:1, 90:1, 91:1, 92:1, 93:1, 94:1, 95:1, 96:1, 97:1, 98:1. 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1 or greater.

The amount of infectious agent may be present in the pooled environmental and biological samples in picogram, nanogram, microgram, milligram, or gram quantities. The amount of infectious agent that is considered high or low depends on the nature of the infectious agent. For viral agents a high amount may be detected in nanogram quantities and a low amount may be detected in pictogram quantities. A higher amount of infectious agent including, in a geographic region, subordinate location, or subordinate space, means that there is more of the infectious agent in that geographic region, subordinate location, or subordinate space, as compared to other geographic regions, subordinate locations, or subordinate spaces. In an embodiment, the amount of an infectious agent refers to a viral load (also known as viral burden), or viral titer, which is a numerical expression of the quantity of virus in a given volume of a sample.

A heat map as disclosed herein may show the amount of infectious agent (e.g., picogram, nanogram, microgram, milligram, or gram quantities of the infectious agent) in a geographic region, a subordinate location, or a subordinate space as compared to another geographic region, subordinate location, or subordinate space, respectively. A geographic region, subordinate location, or subordinate space that has more infectious agent as compared to another geographic region, subordinate location, or subordinate space on the heat map is preferably represented by a more intense color or hue as compared those geographic regions, subordinate locations, or subordinate spaces that have a lesser amount of the infectious agent.

In an embodiment, the virus is SARS-CoV-2. In a further embodiment, SARS-CoV-2 is detected by its RNA including, for example, the N, E, S and RdRP genes. In a still further embodiment, real-time reverse transcription polymerase chain reaction (rRT-PCR) is used to detect SARS-CoV-2 RNA.

The environmental samples may be obtained from air (e.g., including by filters) or physical surfaces. The air sample may be a fluidized swab of air filter or other bioaerosol capture device or impingement medium. The physical surface may be a dry surface such as a door handle, window, mirror, or other surface prone to condensation. The dry surface may also be a sewage, HVAC filter and/or duct, or bathroom surface. Additionally, the physical surface may be a high contact surface such as bed linens, furniture, or clothing. Further, the physical surface may be a sewer pipe and/or water drain. In a preferred embodiment, the environmental samples are obtained from a HVAC system (e.g., filter and/or ducting) and a sewage line for a subordinate location such as a building.

The biological samples may be obtained from subjects directly, by means of swabs, and/or human fluids. Nasopharyngeal swabs and/or oropharyngeal swabs are contemplated for use in the present disclosure. Swabs from both sites may be combined to increase sensitivity. Other biological samples may include deeper respiratory secretions such as sputum and bronchoalveolar fluid. The biological sample may also be a blood, plasma, urine, saliva, or fecal sample.

The environmental samples may be collected at the same time the biological samples are collected or may be collected at a different time.

Additionally, biomarkers (e.g., ethnicity, age, etc.) may be determined for subjects in the one or more subordinate locations or subordinate spaces to determine their risk of infection by the infectious agent.

Environmental and/or biological samples may be processed and/or analyzed (e.g., re-prioritized, re-aggregated, and/or discarded) based on an amount of infectious agent identified and/or quantitated in each sample versus other samples.

Additionally or alternatively, environmental and/or biological samples may be processed and/or analyzed (e.g., re-prioritized, re-aggregated, and/or discarded) based on an additional factor(s) including, for example, occupation, income-level, race/ethnicity, etc. For example, environmental and/or biological samples obtained from subordinate locations or subordinate spaces with a higher amount of infectious agent may be prioritized for analysis versus environmental and/or biological samples obtained from subordinate locations or subordinate spaces with a lower amount of infectious agent. Additionally, for example, environmental and/or biological samples obtained from subordinate locations or subordinate spaces associated with hospitals and/or health care workers may be prioritized for analysis versus environmental and/or biological samples obtained from subordinate locations or subordinate spaces associated with other occupations or workers.

Environmental and/or biological samples may be processed and/or analyzed (e.g., re-prioritized, re-aggregated, and/or discarded) based on an amount of infectious agent identified and/or quantitated in other environmental and/or biological samples. For example, environmental and/or biological samples may be prioritized for analysis where other samples from the same or nearby subordinate locations or subordination spaces were found to have a high amount of infectious agent.

Alternatively, the environmental and/or biological samples may be processed and/or analyzed (e.g., re-prioritized, re-aggregated, and/or discarded) based on a risk score from the subordinate location or subordinate space from which the samples were obtained. For example, samples obtained from a subordinate location or subordinate space with a high risk score may be prioritized for analysis as compared to samples obtained from a subordinate space or subordinate location with a lower risk score. Further, for example, samples obtained from a subordinate space or subordinate location with a low risk score may simply be disregarded including, to save conserve resources.

In an embodiment, the environmental samples are collected at the same time as the biological samples. In an alternative embodiment, the environmental samples are collected at a different time than the biological samples.

In an embodiment, one or more companies collect the environmental and/or biological samples, while another company performs the laboratory work.

The first and the second set of environmental and/or biological samples may be processed and/or analyzed (e.g., re-prioritized, re-aggregated, and/or discarded) based on the risk score from the subordinate location or subordinate space from which the samples were obtained.

Also provided herein is a computing platform for use including, by medical providers or government agencies. The platform may store and analyze data from the pooled environmental samples and pooled biological samples, or information associated with the pooled environmental samples and pooled biological samples and optionally make recommendations related to the risk of viral infection in one or more geographic regions.

Computer systems are also provided having one or more processors and memory storing one or more programs for execution by the one or more processors. Such a system includes memory-storing instructions for causing the computer system to perform any of the methods described herein including a portion of any of the methods disclosed herein.

Features of the embodiments described herein can be implemented in, using, or with the assistance of a computer program product, such as a storage medium (media) or computer readable storage medium (media) having instructions stored thereon/in which can be used to program a processing system to perform any of the features presented herein. The storage medium (e.g., the memory) can include, but is not limited to, high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. In some embodiments, the memory may include one or more storage devices remotely located from the CPU(s). The memory, or alternatively the non-volatile memory device(s) within these memories, comprises a non-transitory computer readable storage medium.

Communication systems as referred to herein optionally communicate via wired and/or wireless communication connections. Communication systems optionally communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. Wireless communication connections optionally use any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (W-Fi) (e.g., IEEE 102.11a, IEEE 102.11ac, IEEE 102.11ax, IEEE 102.11b, IEEE 102.11g and/or IEEE 102.11n), voice over Internet Protocol (VoIP), Wi-MAX, a protocol for e mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol.

Figure 6:
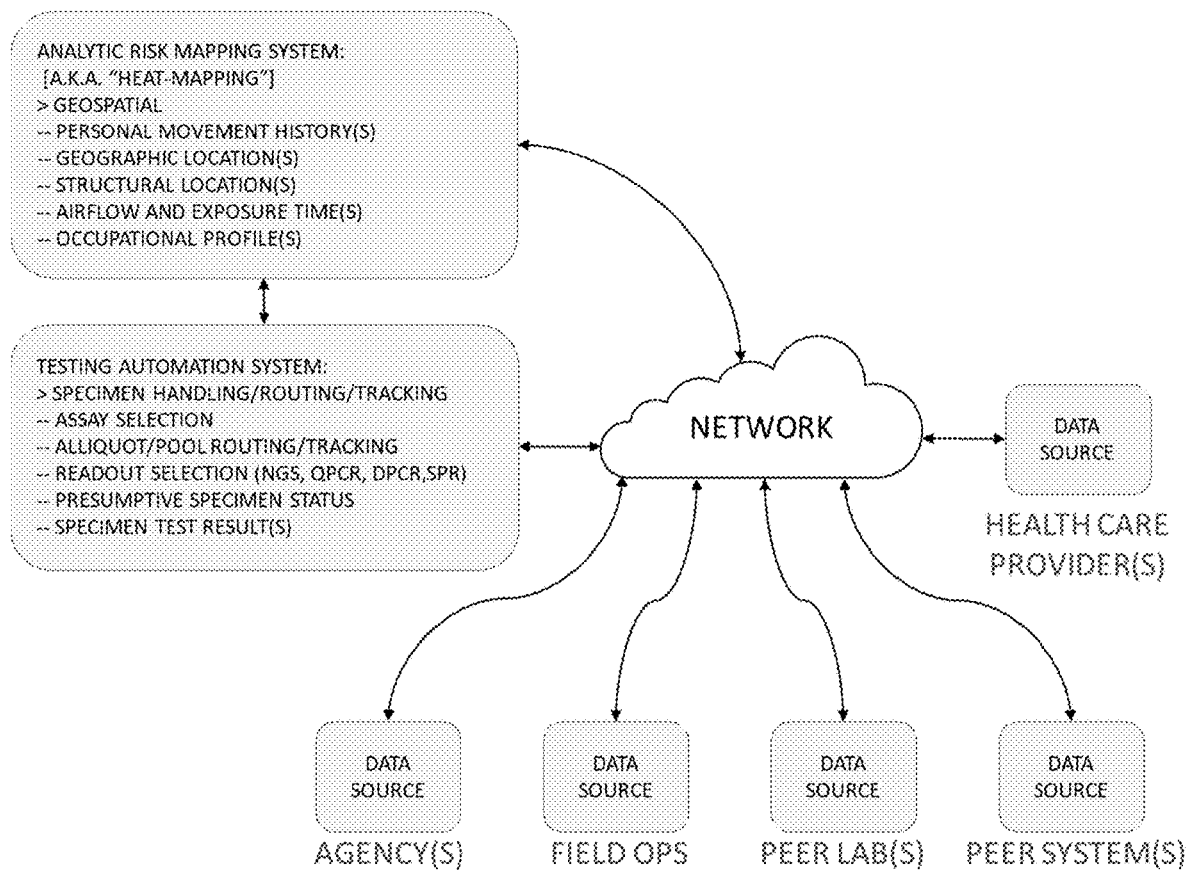
FIG. 6 shows a data flow diagram depicting an embodiment of the disclosure where a contextual analytic risk mapping system (e.g., a heat map) is used to influence an automated testing/screening system or vice versa. The heat map may influence specimen (e.g., an environmental and/or biological sample) handling, routing, processing, tracking, etc.; assay selection; aliquot/pool tracking; readout selection; specimen test results; and presumptive specimen status (e.g., whether it is presumed to be positive or negative for the infectious agent). The heat map and automated testing system may be wired or wireless and may communicate with one another via a network such as a cloud-based network. Further, the network, heat map, and/or automated testing system may pull in data from a number of different sources such governmental agencies (e.g., CDC, FEMA, etc.), field ops (e.g., sample collection teams, quarantine teams, etc.), peer labs (e.g., similar systems in other areas or buildings, or bricks and mortar labs handling overflow or load-levelling), or peer systems (e.g., heat map system and/or testing automation systems affected by the data revisions and results of this heat map or this volume of samples under test) and/or heath care providers (e.g., to inform caregiving hospitals and other facilities about positive samples/patients to inform isolation and/or treatment).

In an exemplary system of the disclosure as shown in FIG. 6 shows an analytic risk mapping system (e.g., a heat map) is used to influence (e.g., effect) an automated testing/screening system or vice versa. The heat map may influence specimen (e.g., an environmental and/or biological sample) handling, routing, processing, tracking, etc.; assay selection; aliquot/pool tracking; readout selection; specimen test results; and presumptive specimen status (e.g., whether it is presumed to be positive or negative for the infectious agent). The heat map and automated testing system may be wired or wireless and may communicate with one another via a network such as a cloud-based network. Further, the network, heat map, and/or automated testing system may pull in data from a number of different sources such governmental agencies (e.g., CDC, FEMA, etc.), field ops (e.g., environmental sample collection, human specimen sample collection, first responders to quarantine a structure or area and control entry or traffic around it/them, medical caregivers that treat and/or transport newly diagnosed patients, coordinating situational management by government agencies or non-governmental organizations, sample collection teams, quarantine teams, etc.), a peer lab (e.g., a third-party system in other areas or buildings, or a conventional clinical testing facility), or a peer system (e.g., a third party risk rating system such as Facebook, Google, Apple, etc.; a heat map system and/or testing automation systems affected by the data revisions and results of the heat map of the disclosure or the volume of samples under test) and/or heath care providers (e.g., to inform caregiving hospitals and other facilities about positive samples/patients to inform isolation and/or treatment).

In an embodiment, a peer lab may be an automated lab and the peer system may be a heat mapping risk-analytic system. In another embodiment, a peer lab is a third party.

In an embodiment, the methods may further comprise administering a medicine to subjects from subordinate locations or subordinate spaces identified as high risk to treat and/or prevent infection by the infectious agent. In another embodiment, the methods may further comprise administering a medicine to subjects from subordinate locations or subordinate spaces identified as moderate or low risk to treat and/or prevent infection by the infectious agent.

The infectious agent may be detected and/or quantitated at the nucleic acid or protein level by any method known in the art including, for example, PCR amplification, NGS or immuno-detection, enzymatic assays, mass-spectrometry, or surface plasmon array. In an embodiment, the infectious agent may be detected and/or quantitated by a point-of-care kit. In another embodiment, the kit may be a real-time PCR kit for the detection of DNA or RNA.

Nucleic acid-based techniques for assessing expression are well known in the art and include, for example, determining the level of RNA in a biological sample. Many expression detection methods use isolated RNA or DNA (see, e.g., Ausubel et al., ed., (1987-1999) Current Protocols in Molecular Biology (John Wiley & Sons, New York). For example, nanopore technology may be employed to detected the DNA or RNA of an infectious agent including, a nanopores set in an arrayed sensor chip.

In some embodiments, sequencing is performed by next generation sequencing. There are several common platforms currently in use.

In some variations, the next generation sequencer is 454 technology developed by Roche. 454 technology uses microbeads to which DNA fragments are captured and clonally amplified by emulsion PCR (emPCR). In various permutations, each bead contains a large number of identical copies of the parent DNA sequence. The beads are deposited on a chip containing multiple wells, with each well containing only one template bead. Each well is addressed by a fiber optic for signal acquisition. 454 technology uses pyrosequencing in which subject nucleotides are flown over the beads containing the clonally amplified DNA fragments, and the template-directed incorporation of a given nucleotide is detected by an enzymatic cascade. The enzymatic cascade uses the pyrophosphate (by-product of base incorporation) to generate a light signal. The light signal intensity is proportional to the number of bases incorporated, such that short homopolymers can be reliably identified. After a wash, the process is repeated with each of the remaining NTPs and the sequence of each DNA fragment is determined from the pattern of light signals produced by each bead. 454 sequencing technology has a read length of 400-600 bases, usually of unequal length. It has around 1M reads per run, does not perform paired reads, and requires approximately 10 hours.

454 sequencers use natural NTPs, and are regarded to have long read length, short run time, high accuracy. They also have complicated sample preparation (e.g. emPCR); low number of reads, and reads of unequal length.

Another example of next generation sequencing is SOLiD (Sequencing by Oligonucleotide Ligation and Detection) (Applied Biosystems). SOLiD uses microbeads to which DNA fragments are captured and clonally amplified by emPCR. The beads are then covalently bound on a glass slide and are microscopically imaged during sequencing. SOLiD technology uses sequencing-by-ligation, in which positions at increasing distance from the end of the molecule are probed with fluorescently-labeled ligation probes. Each probe has two discriminating bases at the end, and each position in the template to be sequenced is probed twice (once at the first position of a ligation probe, then again at the second position of the next ligation probe).

SOLiD sequencing slides can be divided in 4 or 8 sections and separate samples can be loaded on each section, increasing the number of samples that can be run at once. Current SOLiD technology can generate up to 100 Gb of sequence data per run, with a run time of up to 16 days. SOLiD technology generates reads of equal lengths, and it can produce paired end reads. Read length is limited to 2×50 bases for paired end reads and to 60 bases for single end reads. The system can perform up to 1.4 billion reads with microbeads and up to 2.4 billion reads with nanobeads. A run time can take 16 days for 50×50 reads. The system is capable of high throughput, highest accuracy, the possibility of obtaining of paired reads, and has a modular design of the sequencing substrate (slides). The system has complicated sample prep (e.g. emPCR), limited read length, long run time, and results are provided in color space-instead of sequence-space.

Another exemplary next-generation sequencer is provided by Illumina (also known as Solexa technology). Solexa relies on capture primers covalently attached to the surface of glass flow cells, which are used to capture and clonally amplify DNA fragments for sequencing. The clonal amplification occurs on the surface by a process called 'bridge PCR' in which one parent molecule generates a cluster of identical sequences. Illumina technology uses 'sequencing by synthesis' in which fluorescently-labeled, chain-terminating nucleotides are incorporated one at a time in a template-dependent order. After each cycle, the glass surface is microscopically imaged and 4 color pictures are taken, and the base that was incorporated into each cluster is determined; the dye and chain terminator group are removed before the next cycle. The location of each cluster is kept constant for all the cycles.

The Illumina method has a read length of 100 bases (HiSeq), 150 bases (GAllx or MiSeq), 300 bases, 400 bases or more. It can perform up to 600 Million reads/run (GAllx) or 3 Billion reads/run (HiSeq) or 5 Million reads/run (MiSeq), and is capable of paired-end reads. The approximate run time is 14 days for 2×150 reads. The Illumina method has simple sample preparation, relatively long reads, the possibility of obtaining paired-end reads, and includes a modular design of sequencing substrate (lanes on flow cell). The system also has a comparatively long run time.

Other next generation sequencing platforms include Complete Genomics, which uses DNA nanoball sequencing technology in combination with proprietary software to determine the complete genome of submitted samples. The technology is optimized for human genome sequencing projects. The company offers DNA sequencing as a service, and the sequencers are not commercially available.

Pacific Biosciences uses another NGS platform that uses single molecule real time sequencing technology for gene sequencing. The technology in its current form generates very long reads (average 750 bp, longest reads up to 6 kb), but the number of reads is limited ("20 k).

Ion Torrent is another exemplary NGS sequencing platform that uses a technology similar to the 454 technology, with the difference that the incorporated base is detected by a change in pH as opposed to an enzymatic cascade. Ion Torrent technology currently generates reads of about 100 bases, and up to 1M reads per run, with a run time of "2 h. Significant improvements of both read length and throughput are expected for this technology.

Helicos is another NGS sequencing platform that uses true single molecule sequencing (tSMS) technology, in which the template DNA strands are captured on a glass surface by covalently attached capture primers, and are sequenced by the stepwise addition of fluorescently labeled nucleotides, one at a time. The glass surface is imaged after the addition of each base, and the location of each newly incorporated base is recorded. The fluorescent group is then cleaved and the next base is added. Helicos technology can generate billions of reads per run, but the read length is currently limited to about 25 bases.

Isolated DNA/RNA from a sample can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by a gene in the infectious agent. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a gene in the infectious agent. Hybridization of an mRNA with the probe indicates that the gene is being expressed.

An alternative method for determining the level of DNA/RNA in a sample involves the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the disclosure, biomarker expression may be assessed by quantitative fluorogenic RT-PCR (i.e., the TaqMan® System). Such methods typically may utilize pairs of oligonucleotide primers that are specific for the infectious agent. Methods for designing oligonucleotide primers specific for a known sequence are well known in the art.

In one embodiment, amplification-based assays can be used to measure copy number of a gene. In such amplification-based assays, the corresponding nucleic acid sequence acts as a template in an amplification reaction (for example, Polymerase Chain Reaction or PCR). In a quantitative amplification, the amount of amplification product will be proportional to the amount of template in the original sample. Comparison to appropriate controls provides a measure of the copy-number of the gene, corresponding to the specific probe used. The presence of a higher level of amplification product, as compared to a control, is indicative of amplified.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y. The known nucleic acid sequence for the Met (Accession No.: NM 000245) is sufficient to enable one of skill to routinely select primers to amplify any portion of the gene.

Real time PCR is another amplification technique that can be used to determine gene copy levels or levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For gene copy levels, total genomic DNA is isolated from a sample. For mRNA levels, mRNA is extracted from tumor and normal tissue and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-$10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

A TaqMan-based assay also can be used to quantify MET polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification.

Other suitable amplification methods include, but are not limited to ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc.

In another embodiment of the present disclosure, a protein may be detected. A preferred agent for detecting a protein of the disclosure is an antibody capable of binding to such a protein or a fragment thereof, preferably an antibody with a detectable label. Antibodies can be polyclonal, or more preferably, monoclonal. An intact antibody, or a fragment or derivative thereof can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that may be directly labeled. Examples of indirect labeling include detection of a primary antibody using a fluorescently labeled secondary antibody and end-labeling of a DNA probe with biotin such that it can be detected with fluorescently labeled streptavidin.

Antibody fragments may comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) Protein Eng. 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and may be still capable of cross-linking antigen.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesteRase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

In regard to detection of antibody staining in the immunocytochemistry methods of the disclosure, there also exist in the art, video-microscopy and software methods for the quantitative determination of an amount of multiple molecular species (e.g., biomarker proteins) in a biological sample wherein each molecular species present may be indicated by a representative dye marker having a specific color. Such methods are also known in the art as a colorimetric analysis methods. In these methods, video-microscopy may be used to provide an image of the biological sample after it has been stained to visually indicate the presence of a particular biomarker of interest. Some of these methods, such as those disclosed in U.S. patent application Ser. Nos. 09/957,446 and 10/057,729, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that may be deconstructed into its component color parts.

The antibodies used to practice the disclosure are selected to have high specificity for a protein from the infectious agent. Methods for making antibodies and for selecting appropriate antibodies are known in the art (see, e.g., Celis, ed. (in press) *Cell Biology & Laboratory Handbook,* 3rd edition (Academic Press, New York)).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present disclosure.

One skilled in the art will know many other suitable carriers for binding antibody or antigen, and will be able to adapt such support for use with the present disclosure. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies.

Environmental and/or biological samples from a geographic region, subordinate location, or subordinate space may be pooled and the amount of infectious agent in the samples determined about every 30 seconds, about every 1 minute, about every 2 minutes, about every 3 minutes, about every 4 minutes, about every 5 minutes, about every 10 minutes, about every 15 minutes, about every 20 minutes, about every 25 minutes, about every 30 minutes, about every 35 minutes, about every 40 minutes, about every 45 minutes, about every 50 minutes, about every 55 minutes, about every 1 hour, about every 2 hours, about every 3 hours, about every 4 hours, about every 5 hours, about every 6 hours, about every 7 hours, about every 8 hours, about every 9 hours, about every 10 hours, about every 11 hours, about every 12 hours, about every 13 hours, about every 14 hours, about every 15 hours, about every 16 hours, about every 17 hours, about every 18 hours, about every 19 hours, about every 20 hours, about every 21 hours, about every 22 hours, about every 23 hours, about every 24 hours, about every 2 days, about every 3 days, about every 4 days, about every 5 days, about every 6 days, about every 7 days, about every 2 weeks, about every 3 weeks, about every 4 weeks, about every 2 months, about every 3 months, about every 4 months, about every 5 months, about every 6 months, about every 7 months, about every 8 months, about every 9 months, about every 10 months, about every 11 months, about every 12 months, about every 2 years, about every 3 years, about every 4 years, or about every 5 years. In another embodiment, environmental and/or biological samples are pool and the amount of infectious agent in the samples is determined continuously in real-time.

Illustration of Subject Technology as Clauses

Various examples of aspects of the disclosure are described as numbered clauses (1, 2, 3, etc.) for convenience. These are provided as examples, and do not limit the subject technology.

Clause 1.) A method for screening biological samples obtained from subjects at a geographic region for an infectious agent, the method comprising:
dividing the geographic region into one or more subordinate locations, or dividing the one or more subordinate locations into one or more subordinate spaces;
pooling environmental samples obtained within each of the one or more subordinate locations or subordinate spaces;
pooling biological samples obtained from subjects within each of the one or more subordinate locations or subordinate spaces;
measuring an amount of the infectious agent in the pooled environmental samples and pooled biological samples for each of the one or more subordinate locations or subordinate spaces;
assigning an risk score to each of the one or more subordinate locations or subordinate spaces based on the amount of infectious agent in the pooled environmental samples and the pooled biological samples in a subordinate location or subordinate space as compared to each other subordinate location or subordinate space; and
screening biological samples and/or environmental samples from subordinate locations or subordinate spaces that have a higher risk score before screening biological samples and/or environmental samples from subordinate locations or subordinate spaces that has a lower risk score.

Clause 2.) The method of Clause 1, wherein the infectious agent is a virus or a bacterium.

Clause 3.) The method of Clause 2, wherein the virus is SARS-CoV-2.

Clause 4.) The method of Clause 1, wherein the environmental sample is a bioaerosol.

Clause 5.) The method of Clause 1, wherein the environmental and/or biological samples are geo-tagged.

Clause 6.) The method of Clause 1, wherein the environmental and/or biological samples are barcoded.

Clause 7.) The method of Clause 1, wherein the environmental and/or biological samples are pooled at a ratio of about 2:1 to about 10,000:1.

Clause 8.) The method of Clause 1, wherein the environmental and/or biological samples are pooled at a ratio of about 2:1 to about 1,000:1.

Clause 9.) The method of Clause 1, wherein the environmental and/or biological samples are pooled at a ratio of about 2:1 to about 100:1.

Clause 10.) The method of Clause 1, wherein a subject is considered within a subordinate location or subordinate space if the subject resides, travels through, and/or works in the subordinate location or subordinate space.

Clause 11.) The method of Clause 1, wherein the environmental and/or biological samples are analyzed by a high-throughput method.

Clause 12.) The method of Clause 11, wherein the environmental and/or biological samples are analyzed by high-throughput PCR.

Clause 13.) The method of Clause 1, wherein the one or more subordinate locations or subordinate spaces are adjacent to one another.

Clause 14.) The method of Clause 1, wherein the geographic region is a country, state, county, city, or neighborhood.

Clause 15.) The method of Clause 1, wherein the one or more subordinate locations include one or more counties, cities, or city blocks.

Clause 16.) The method Clause 1, wherein the one or more subordinate locations are a city block, multiple city blocks, a house(s) or a building(s).

Clause 17.) The method of Clause 1, wherein the one or more subordinate locations are buildings associated with a specific type of business or trade.

Clause 18.) The method of Clause 1, wherein the one or more subordinate locations are buildings having a common structural feature.

Clause 19.) The method of Clause 1, wherein the one or more subordinate locations have a longitude and a latitude or other GPS coordinate scheme.

Clause 20.) The method of Clause 1, wherein the environmental samples are air samples.

Clause 21.) The method of Clause 1, wherein the environmental samples are from a dry or a wet surface.

Clause 22.) The method of Clause 21, wherein the dry surface is a door handle.

Clause 23.) The method of Clause 1, wherein environmental and/or biological samples are pooled from 2-1,000 subordinate locations or subordinate spaces.

Clause 24.) The method of Clause 1, wherein environmental and/or biological samples are pooled from 10-100 subordinate locations or subordinate spaces.

Clause 25.) A method for pooling biological and/or environmental samples, the method comprising:
  a.) dividing the geographic region into one or more subordinate locations or dividing the one or more subordinate locations into one or more subordinate spaces;
  b.) pooling a first set of environmental samples obtained within each of the one or more subordinate locations or subordinate spaces and pooling a first set of biological samples obtained from subjects within each of the one or more subordinate locations or subordinate spaces;
  c.) measuring an amount of an infectious agent in the first set of pooled environmental samples and pooled biological samples for each of the one or more subordinate locations or subordinate spaces;
  d.) assigning an risk score to each of the one or more subordinate locations or subordinate spaces based on the amount of infectious agent in the first set of pooled environmental samples and the pooled biological samples in each subordinate location or subordinate space as compared to each other subordinate location or subordinate space;
  e.) pooling a second set of environmental samples and biological samples from the one or more subordinate locations or subordinate spaces, wherein the second set of environmental samples and biological samples are pooled at a higher ratio from subordinate locations or subordinate spaces assigned a lower risk score as compared to subordinate locations or subordinate spaces assigned a higher risk score; and
  f.) optionally repeating steps b. through e. to repeatedly update the risk score for each of the one or more subordinate locations or subordinate spaces.

Clause 26.) The method of Clause 25, wherein the infectious agent is a virus or a bacterium.

Clause 27.) The method of Clause 26, wherein the virus is SARS-CoV-2.

Clause 28.) The method of Clause 25, wherein the geographic region is a country, state, county, city, or neighborhood.

Clause 29.) The method of Clause 28, wherein the geographic region is a state.

Clause 30.) The method of Clause 28, wherein the geographic region is a city.

Clause 31.) The method of Clause 25, wherein the one or more subordinate locations include one or more counties, cities, or city blocks.

Clause 32.) The method of Clause 25, wherein the first and the second set of environmental samples includes a bioaerosol.

Clause 33.) The method of Clause 25 further comprising screening biological samples from subordinate locations or subordinate spaces that have a higher risk score before screening biological samples from subordinate locations or subordinate spaces that have a lower risk score.

Clause 34.) The method of Clause 25, wherein the one or more subordinate locations or subordinate spaces are scored on a scale of 1 to 10 with a score of 1 corresponding to a low risk score and a score of 10 corresponding to a high risk score.

Clause 35.) The method of Clause 25, wherein the one or more subordinate locations or subordinate spaces are scored from low, medium, or high with a score of low corresponding to a low risk score and a score of high corresponding to a high risk score.

Clause 36.) The method of Clause 25, wherein the first and the second set of environmental and/or biological samples are re-prioritized, re-aggregated, and/or discarded based on the risk score from the subordinate location or subordinate space from which the samples were obtained.

Clause 37.) The method of Clause 25, wherein the first set and the second set of environmental and/or biological samples are geo-tagged.

Clause 38.) The method of Clause 25, wherein the first set and the second set of environmental and/or biological samples are barcoded.

Clause 39.) The method of Clause 25, wherein the first set and the second set of environmental and/or biological samples are pooled at a ratio of about 2:1 to about 10,000:1.

Clause 40.) The method of Clause 25, wherein the first set and the second set of environmental and/or biological samples are pooled at a ratio of about 2:1 to about 1,000:1.

Clause 41.) The method of Clause 25, wherein the first set and the second set of environmental and/or biological samples are pooled at a ratio of about 2:1 to about 100:1.

Clause 42.) The method of Clause 25, wherein the subjects are considered within a subordinate location or subordinate space where they reside, travel through, and/or work in the subordinate location or subordinate space.

Clause 43.) The method of Clause 25, wherein the first set and the second set of environmental and/or biological samples are analyzed by a high-throughput method.

Clause 44.) The method of Clause 43, wherein the first set and the second set of environmental and/or biological samples are analyzed by high-throughput PCR.

Clause 45.) The method of Clause 25, wherein the one or more subordinate locations are adjacent to one another.

Clause 46.) The method Clause 25, wherein the one or more subordinate locations are a city block, multiple city blocks, a house(s), or a building(s).

Clause 47.) The method of Clause 25, wherein the one or more subordinate locations are buildings associated with a specific business or trade.

Clause 48.) The method of Clause 25, wherein the one or more subordinate locations are buildings having a common structural feature.

Clause 49.) The method of Clause 25, wherein the one or more subordinate locations have a longitude and a latitude or other GPS coordinate scheme.

Clause 50.) The method of Clause 25, wherein the first and second set of environmental samples are air samples.

Clause 51.) The method of Clause 25, wherein the first and second set of environmental sample are from a dry or a wet surface.

Clause 52.) The method of Clause 51, wherein the dry surface is a door handle.

Clause 53.) The method of Clause 25, wherein the first and second set of environmental and/or biological samples are pooled from 1-1,000 subordinate locations or subordinate spaces.

Clause 54.) The method of Clause 25, wherein the first and second set of environmental and/or biological samples are pooled from 10-100 subordinate locations or subordinate spaces.

Clause 55.) A method of determining a risk of an infection with an infectious agent for a subject in a subordinate location of a geographic region, the method comprising,
  generating a heat map of the amount of infectious agent at one or more subordinate locations within the geographic region, wherein the heat map is generated by:
  pooling environmental samples and biological samples obtained within each of the one or more subordinate locations;
  measuring an amount of the infectious agent in the pooled environmental samples and pooled biological samples for each of the one or more subordinate locations, and
  assigning each of the one or more subordinate locations a risk score based on the amount of infectious agent in the pooled environmental samples and the pooled biological samples in each of the one or more subordinate locations as compared to each other subordinate location; and
  determining the risk of infection with the infectious agent for the subject based on the risk score assigned to the subordinate location of the individual.

Clause 56.) The method of Clause 55 further comprising clearing or re-opening one or more subordinate locations based on the risk score.

Clause 57.) The method of Clause 55, wherein the infectious agent is SARS-CoV-2.

Clause 58.) The method of Clause 55, wherein the geographic region is a country, state, county, city, or neighborhood.

Clause 59.) The method of Clause 58, wherein the geographic region is a city.

Clause 60.) The method of Clause 55, wherein the one or more subordinate locations include one or more counties, cities, or city blocks.

Clause 61.) The method of Clause 55, wherein the environmental sample includes a bioaerosol.

Clause 62.) The method of Clause 57, wherein the subject has not previously been infected with the virus.

Clause 63.) The method of Clause 55 further comprising screening biological samples from a subordinate location that has a higher risk score before screening biological samples from a subordinate location that has a lower risk score.

Clause 64.) The method of Clause 55, wherein a subordinate location is scored on a scale of 1 to 10 with a score of 1 corresponding to a low risk score and a score of 10 corresponding to a high risk score.

Clause 65.) The method of Clause 55, wherein the pooling ratio is higher for subordinate locations with a lower risk score than subordinate locations having a higher risk score.

Clause 66.) The method of Clause 55, wherein the environmental and/or biological samples are re-prioritized, re-aggregated, and/or discarded based on the risk score from the subordinate location from which they were obtained.

Clause 67.) The method of Clause 55, wherein the environmental and/or biological samples are geo-tagged.

Clause 68.) The method of Clause 55, wherein the environmental and/or biological samples are barcoded.

Clause 69.) The method of Clause 55, wherein the environmental and/or biological samples are pooled at a ratio of about 2:1 to about 10,000:1.

Clause 70.) The method of Clause 55, wherein the environmental and/or biological samples are pooled at a ratio of about 2:1 to about 1,000:1.

Clause 71.) The method of Clause 55, wherein the environmental and/or biological samples are pooled at a ratio of about 2:1 to about 100:1.

Clause 72.) The method of Clause 55, wherein a subject is considered in a subordinate location if the subject resides, travels through, and/or works in the subordinate location.

Clause 73.) The method of Clause 55, wherein the environmental and/or biological samples are analyzed by a high-throughput method.

Clause 74.) The method of Clause 73, wherein the environmental and/or biological samples are analyzed by high-throughput PCR.

Clause 75.) The method of Clause 55, wherein the one or more subordinate locations are adjacent to one another.

Clause 76.) The method of Clause 55, wherein the one or more subordinate locations are not adjacent to one another.

Clause 77.) The method of Clause 55, wherein the one or more subordinate locations are buildings associated with a certain a business or trade.

Clause 78.) The method of Clause 55, wherein the one or more subordinate locations are buildings having a common structural feature.

Clause 79.) The method of Clause 55, wherein the one or more subordinate locations have a longitude and a latitude or other GPS coordinate scheme.

Clause 80.) The method of Clause 55, wherein the environmental samples are air samples.

Clause 81.) The method of Clause 55, wherein the environmental sample are from a dry or a wet surface.

Clause 82.) The method of Clause 81, wherein the dry surface is a door handle.

Clause 83.) The method of Clause 55, wherein environmental and/or biological samples are pooled from 1-1,000 subordinate locations.

Clause 84.) The method of Clause 55, wherein environmental and/or biological samples are pooled from 10-100 subordinate locations.

Clause 85.) A method of screening biological samples obtained from subjects at one or more subordinate locations within a geographic region, the method comprising,
  determining a number of subjects infected with a virus at the one or more subordinate locations to generate a first heat-map based on a risk score for the one or more subordinate locations;

generating a second heat map of an amount of virus in each of the one or more subordinate locations wherein the heat map is generated by:
  pooling environmental samples and biological samples obtained within each of the one or more subordinate locations;
  measuring an amount of virus in the pooled environmental samples and pooled biological samples for each of the one or more subordinate locations, and
  assigning each of the one or more subordinate locations a second risk score based on the amount of virus in the pooled environmental samples and the pooled biological samples in each subordinate location as compared to each other subordinate location; and
  comparing the first heat map to the second heat map;
  identifying changes in the risk score in the one or more subordinate locations between the first heat map and the second heat map; and
  changing a screening protocol in any subordinate locations in which the risk score is different between the first heat map and the second heat map.

Clause 86.) A method of screening biological samples obtained from subjects at one or more subordinate locations within a geographic region, the method comprising:
  a.) generating a first heat map of an amount of virus in each of a first group one or more subordinate locations wherein the heat map is generated by:
    pooling a first set of environmental samples and biological samples obtained within each of the one or more subordinate locations in the first group;
    measuring an amount of virus in the first set of pooled environmental samples and pooled biological samples for each of the one or more subordinate locations in the first group, and
    assigning each of the one or more subordinate locations in the first group a first risk score based on the amount of virus in the first set of pooled environmental samples and the pooled biological samples in each subordinate location in the first group as compared to each other subordinate location in the first group; and
  b.) generating a second heat map of an amount of virus in each of a second group of one or more subordinate locations wherein the heat map is generated by:
    pooling a second set of environmental samples and biological samples obtained within each of the one or more subordinate locations in the second group;
    measuring an amount of virus in the second set of pooled environmental samples and pooled biological samples for each of the one or more subordinate locations in the second group, and
    assigning each of the one or more subordinate locations in the second group a second risk score based on the amount of virus in the pooled environmental samples and the pooled biological samples in each subordinate location in the second group as compared to each other subordinate location in the second group; and
  c.) comparing the first heat map to the second heat map;
  d.) identifying changes in the risk score in the one or more subordinate locations between the first heat map and the second heat map; and
  e.) changing a screening protocol in any subordinate locations in which the risk score is different between the first heat map and the second heat map; and
  f.) optionally repeating steps a. through e.

Clause 87.) The method of Clause 86, wherein the virus is SARS-CoV-2.

Clause 88.) A heat map generated by the method of Clause 86.

Clause 89.) The method of Clause 86, wherein the change in the screening protocol includes prioritizing for screening biological samples from subordinate locations assigned a higher risk score over biological samples from subordinate locations assigned a lower risk score.

Clause 90.) The method of Clause 86, wherein the change in the screening protocol includes revising the risk score of other biological samples already in a screening process.

Clause 91.) The method of Clause 86, wherein the change in the screening protocol includes discarding samples.

Clause 92.) A method for reducing costs associated with screening a population of subjects for a infection with an infectious agent in a geographic region, the method comprising:
  a.) dividing the geographic region into a first group of one or more subordinate locations;
  b.) pooling a first set of environmental samples and biological samples obtained from the first group of one or more subordinate locations;
  c.) measuring an amount of virus in the first set of pooled environmental samples and pooled biological samples for each of the first group of one or more subordinate locations;
  d.) assigning a risk score to each of the first group of one or more subordinate locations based on the amount of virus in the first set of pooled environmental samples and biological samples in each subordinate location in the first group as compared to each other subordinate location in the first group; and
  e.) pooling a second set of environmental samples and biological samples from a second group of one or more subordinate locations in the geographic region, wherein samples are pooled at a higher ratio from subordinate locations in the first group assigned a low risk score versus subordinate locations identified as having a higher risk score,
  wherein pooling the environmental samples and biological samples reduces costs associated with screening the population of subjects.

Clause 93.) The method of Clause 92, wherein the virus is SARS-CoV-2.

Clause 94.) The method of Clause 92, wherein the first group of one or more subordinate locations is the same as the second group of one or more subordinate locations.

EXAMPLES

Example 1: Screening Environmental and Biological Samples in Subordinate Locations within a City to Determine a Risk of Infection from SARS-CoV-2

Seattle is divided into subordinate locations where each city block constitutes a subordinate location. Next, a first set of environmental samples is obtained from air samples, light poles, and mailboxes in each of the one or more subordinate locations. The environmental samples are then pooled for each subordinate location. Nasal swabs are then taken from subjects that work and/or reside in each of the subordinate locations. The swabs are then pooled for each of the subordinate locations. Subsequently, the amount of SARS-CoV-2 is quantitated in each of the pooled environmental samples and pooled nasal swabs for each of the one or more subordinate locations. Next, the each of the subordinate locations is assigned an infectious agent risk score based on the amount of SARS-CoV-2 in the first set of pooled environmental samples and the pooled nasal swabs in each subordinate location as compared to each other subordinate location.

Figure 5:
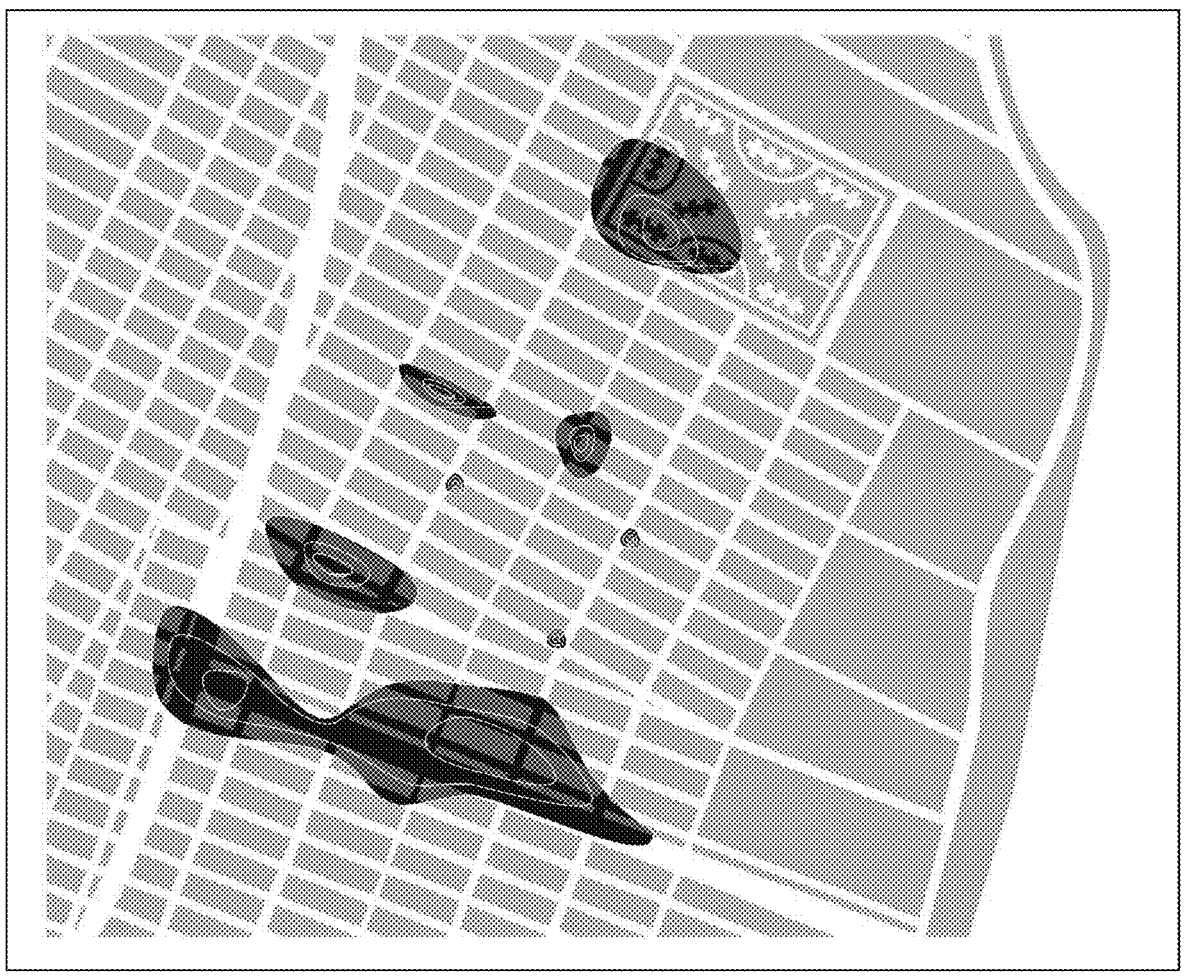
FIG. 5 shows a partial map of a city with subordinate locations identified as a low risk for infection of SARS-CoV-2 shaded in light grey and subordinate locations identified as high risk for infection of SARS-CoV-2 shaded in dark grey.

Subordinate locations including, a housing complex, a travel/transportation corridor, a city block where homeless tend to aggregate and/or make camp displayed a higher amount of SARS-CoV-2 versus the surrounding residential neighborhood (see FIG. 5 showing a heat map with darker areas indicating a higher amount of SARS-CoV-2 and lighter grey area indicating a lower amount of SARS-CoV-2. The darker areas on the heat map are assigned a risk score of high and the lighter grey areas are assigned a risk score of low.

A second set of environmental samples and nasal swabs is obtained from the same subordinate locations in which the first set is obtained. However, the second set of samples is pooled at a higher ratio from subordinate locations assigned a lower infectious agent risk score as compared to subordinate locations assigned a higher infectious agent risk score based on the amount of SARS-CoV-2 measured in the first set of samples. Optionally the method is repeated to update the infectious agent risk score for each of the one or more subordinate locations.

Example 2: Generating a Heat Map for Risk of SARS-CoV-2 Infection in Subordinate Spaces within a City New York is divided into subordinate locations where each city block constitutes a subordinate location. The city blocks are further divided into subordinate spaces where the spaces are common areas within a long-term care facility (i.e., hallways labeled hallway A and B, entrances labeled entrance A, and B, an exit labeled exit A, meeting spaces labeled meeting space A and B). Next, a first set of environmental samples is obtained from air samples, door knobs, floors, HVAC ducting in each of the one or more subordinate locations. The environmental samples are then pooled for each subordinate location. Nasal swabs are then taken from subjects that pass through each of the subordinate locations. The swabs are then pooled for each of the subordinate locations.

Subsequently, the amount of SARS-CoV-2 is quantitated in each of the pooled environmental samples and pooled nasal swabs for each of the one or more subordinate locations. The amount of virus in the pooled samples broke down as follows: entrance A (12 pg)<meeting space A (25 pg)<exit A (50 ng)<meeting space B (85 ng)<hallway A (50 pg)<meeting space A (100 vg)<entrance B (225 pg). Thus, entrance B has the largest amount of virus (225 pg) while entrance A (25 pg) had the smallest amount of virus. Each of the subordinate spaces is then assigned a risk score based on the amount of virus in that space as compared to each other subordinate space. For example, spaces with an amount of virus in picogram amounts are assigned a low risk score, spaces with amounts of virus in nanogram amounts are assigned a moderate risk score and space with microgram amounts are assigned a high risk score.

A second set of environmental samples and nasal swabs is obtained from the same subordinate spaces in which the first set is obtained. However, the second set of samples is pooled at a higher ratio from subordinate locations assigned a lower risk score as compared to subordinate locations assigned a higher risk score based on the amount of virus measured in the first set of samples. For example, the pooling ratio is 100:1 for locations designated as low risk versus spaces designated as high risk.

Although the disclosure has been described and illustrated with a certain degree of particularity, it is understood that the present disclosure has been made only by way of example, and that numerous changes in the combination and arrangement of parts can be resorted to by those skilled in the art without departing from the scope of the disclosure, as hereinafter claimed.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified samples or steps and those that do not materially affect the basic and novel characteristic(s). Embodiments of the disclosure so claimed are inherently or expressly described and enabled herein.

Thus, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. Method claims may be provided to present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary and Brief Description of the Drawings are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims reflect, inventive subject matter lies in less than all features of a single disclosed configuration or operation.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A method for regulating a screening order for screening environmental and/or biological samples associated with a geographic region for an infectious agent, the method comprising:
    dividing the geographic region into one or more subordinate locations, or dividing the one or more subordinate locations into one or more subordinate spaces;
    pooling environmental samples obtained within each of the one or more subordinate locations or subordinate spaces at a pooling ratio of about 2:1 to about 100:1;
    pooling biological samples obtained from subjects within each of the one or more subordinate locations or subordinate spaces at a pooling ratio of about 2:1 to about 100:1;
    measuring an amount of the infectious agent in the pooled environmental and/or biological samples for each of the one or more subordinate locations or subordinate spaces;
    assigning a risk score to each of the one or more subordinate locations or subordinate spaces based on the amount of infectious agent in the pooled environmental and/or biological samples in a subordinate location or subordinate space as compared to each other subordinate location or subordinate space;
    determining a screening order for screening individual biological and/or environmental samples from each of the one or more subordinate locations or subordinate spaces, including screening individual biological and/or environmental samples from subordinate locations or subordinate spaces that have a higher risk score before screening individual biological and/or environmental samples from subordinate locations or subordinate spaces that has a lower risk score; and
    screening individual biological and/or environmental samples from the one or more subordinate locations or subordinate spaces in accordance with the screening order.

2. The method of claim 1, wherein the infectious agent is a virus or a bacterium.

3. The method of claim 2, wherein the virus is SARS-CoV-2.

4. The method of claim 1, wherein a subject is considered within a subordinate location or subordinate space if the subject resides, travels through, and/or works in the subordinate location or subordinate space.

5. The method of claim 1, wherein the geographic region is a country, state, county, city, or neighborhood.

6. The method of claim 1, wherein the one or more subordinate locations include one or more counties, cities, or city blocks.

7. The method claim 1, wherein the one or more subordinate locations are a city block, multiple city blocks, a house(s) or a building(s).

8. The method of claim 1, wherein the environmental samples are air samples.

9. The method of claim 1, wherein the environmental samples are from a dry or a wet surface.

10. The method of claim 1, wherein environmental and/or biological samples are pooled from 10-100 subordinate locations or subordinate spaces.

11. The screening method of claim 1, wherein the geographic location is the earth and the one or more subordinate locations are a moving vessel.

12. A method for regulating pooling ratios for pooling environmental and/or biological samples associated with a geographic region, the method comprising:
   a.) dividing the geographic region into one or more subordinate locations or dividing the one or more subordinate locations into one or more subordinate spaces;
   b.) pooling a first set of environmental samples obtained within each of the one or more subordinate locations or subordinate spaces at a first pooling ratio of about 2:1 to about 100:1 and pooling a first set of biological samples obtained from subjects within each of the one or more subordinate locations or subordinate spaces at a first pooling ratio of about 2:1 to about 100:1;
   c.) measuring an amount of an infectious agent in the first set of pooled environmental and/or biological samples for each of the one or more subordinate locations or subordinate spaces;
   d.) assigning a risk score to each of the one or more subordinate locations or subordinate spaces based on the amount of infectious agent in the first set of pooled environmental and/or biological samples in each subordinate location or subordinate space as compared to each other subordinate location or subordinate space;
   e.) determining a second pooling ratio, higher than the first pooling ratio, for pooling environmental and/or biological samples associated with subordinate locations or subordinate spaces assigned a lower risk score as compared to environmental and/or biological samples associated with subordinate locations or subordinate spaces assigned a higher risk score; and
   f.) pooling a second set of environmental and/or biological samples from the one or more subordinate locations or subordinate spaces, wherein the second set of environmental and/or biological samples are pooled at the second pooling ratio for subordinate locations or subordinate spaces assigned the lower risk score.

13. The method of claim 12, wherein the infectious agent is a virus or a bacterium.

14. The method of claim 13, wherein the virus is SARS-CoV-2.

15. The method of claim 12, wherein the geographic region is a country, state, county, city, or neighborhood.

16. The method of claim 12, wherein the one or more subordinate locations include one or more counties, cities, or city blocks.

17. The method of claim 12 further comprising screening biological samples from subordinate locations or subordinate spaces that have a higher risk score before screening biological samples from subordinate locations or subordinate spaces that have a lower risk score.

18. The method of claim 12, wherein the first and the second set of environmental and/or biological samples are re-prioritized, re-aggregated, and/or discarded based on the risk score from the subordinate location or subordinate space from which the samples were obtained.

19. A method of regulating a screening protocol for screening environmental and/or biological samples associated with one or more subordinate locations within a geographic region, the method comprising,
   determining a number of subjects infected with a virus at the one or more subordinate locations;
   generating a first heat map based on a first risk score for the one or more subordinate locations, wherein the risk score is based on the number of subjects infected with the virus;
   generating a second heat map of an amount of virus in each of the one or more subordinate locations wherein the heat map is generated by:
      pooling environmental and/or biological samples obtained within each of the one or more subordinate locations at a pooling ratio of about 2:1 to about 100:1;
      measuring an amount of virus in the pooled environmental and/or biological samples for each of the one or more subordinate locations, and
      assigning each of the one or more subordinate locations a second risk score based on the amount of virus in the pooled environmental and/or biological samples in each subordinate location as compared to each other subordinate location; and
   comparing the first heat map to the second heat map;
   identifying, based on the comparing, differences between the first risk score and the second risk score in the one or more subordinate locations between the first heat map and the second heat map; and
   changing a screening protocol in any subordinate locations in which the second risk score is different from the first risk score
   wherein changing the screening protocol includes (i) prioritizing screening environmental and/or biological samples from subordinate locations assigned a higher risk score over environmental and/or biological samples from subordinate locations assigned a lower risk score, (ii) revising a risk score of other environmental and/or biological samples already in a screening process, and/or (iii) discarding samples.

20. The method of claim 19, wherein the virus is SARS-CoV-2.

21. A non-transitory machine-readable storage medium comprising machine-readable instructions for causing a processor to execute the method of claim 1.

22. A biological sample screening system comprising:
   a memory configured to store instructions; and
   one or more processors configured to execute one or more instructions stored in the memory to perform the method of claim 1.

* * * * *